United States Patent
Sterling

(10) Patent No.: US 7,201,728 B2
(45) Date of Patent: *Apr. 10, 2007

(54) ANATOMICALLY DESIGNED ORTHOPEDIC KNEE BRACE

(76) Inventor: Shane Sterling, 1555 Magnolia Blvd. W., Seattle, WA (US) 98199

( * ) Notice: Subject to any disclaimer, the term of this patent is extended or adjusted under 35 U.S.C. 154(b) by 0 days.

This patent is subject to a terminal disclaimer.

(21) Appl. No.: 10/608,696

(22) Filed: Jun. 26, 2003

(65) Prior Publication Data

US 2004/0054311 A1    Mar. 18, 2004

Related U.S. Application Data

(63) Continuation-in-part of application No. 10/187,008, filed on Jun. 28, 2002, now Pat. No. 6,969,364.

(60) Provisional application No. 60/417,819, filed on Oct. 11, 2002.

(51) Int. Cl.
*A61F 5/00* (2006.01)
(52) U.S. Cl. .......................................... 602/16; 602/26
(58) Field of Classification Search .................. 602/26, 602/16, 5, 23
See application file for complete search history.

(56) References Cited

U.S. PATENT DOCUMENTS

| | | | |
|---|---|---|---|
| 1,390,915 A | 9/1921 | Loth | |
| 4,463,751 A * | 8/1984 | Bledsoe | 602/16 |
| 4,475,543 A * | 10/1984 | Brooks et al. | 602/19 |
| 4,723,539 A | 2/1988 | Townsend | 128/80 C |
| 4,751,920 A | 6/1988 | Mauldin et al. | 128/80 C |
| 4,886,054 A | 12/1989 | Castillo et al. | 128/80 F |
| 5,009,223 A | 4/1991 | DeFonce | 128/80 C |
| 5,107,824 A | 4/1992 | Rogers et al. | 602/16 |
| 5,119,805 A * | 6/1992 | Cadoret | 602/16 |
| 5,230,697 A | 7/1993 | Castillo et al. | 602/16 |
| 5,286,250 A | 2/1994 | Meyers et al. | 602/16 |
| 5,632,725 A | 5/1997 | Silver et al. | 602/26 |
| 5,792,086 A | 8/1998 | Bleau et al. | 602/26 |
| 5,797,864 A * | 8/1998 | Taylor | 602/26 |

* cited by examiner

*Primary Examiner*—Teena Mitchell
*Assistant Examiner*—Shumaya B. Ali
(74) *Attorney, Agent, or Firm*—Jeffrey J. King; Black Lowe & Graham

(57) ABSTRACT

An orthopedic knee brace provides an apparatus for accurately prescribing the anatomical motion of the human knee. The orthopedic knee brace is used for treatment and rehabilitation following surgery to the knee, protection for a surgically repaired knee, and protection for an uninjured knee, among other applications. The orthopedic knee brace actively prescribes asymmetric three-dimensional anatomic motion in six degrees of freedom of the wearer's knee. The rigid connections between the thigh and calf engaging members and the medial and lateral hinges provide the ability of the orthopedic knee brace to prescribe asymmetric three-dimensional anatomic motion in six degrees of freedom by actively prescribing flexion and extension, abduction and adduction, internal/external rotation, anterior/posterior translation, medial/lateral translation, and proximal/distal translation between a femur and a tibia of a wearer's leg. In alternate embodiments a single-hinge brace design is provided for treatment and prevention of osteoarthritis and other joint diseases and conditions.

44 Claims, 19 Drawing Sheets

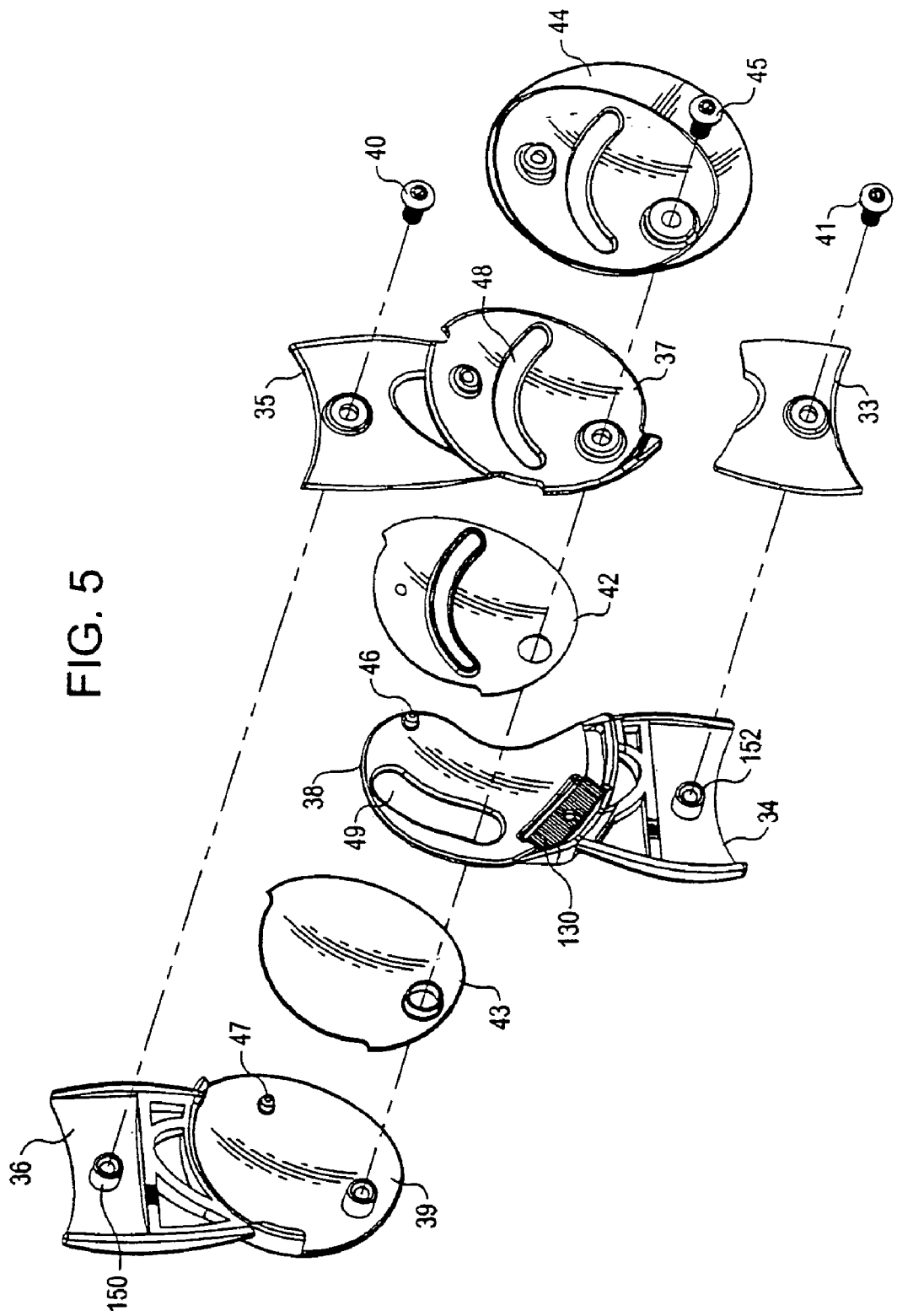

0 DEGREES OF FLEXION

20 DEGREES OF FLEXION

40 DEGREES OF FLEXION

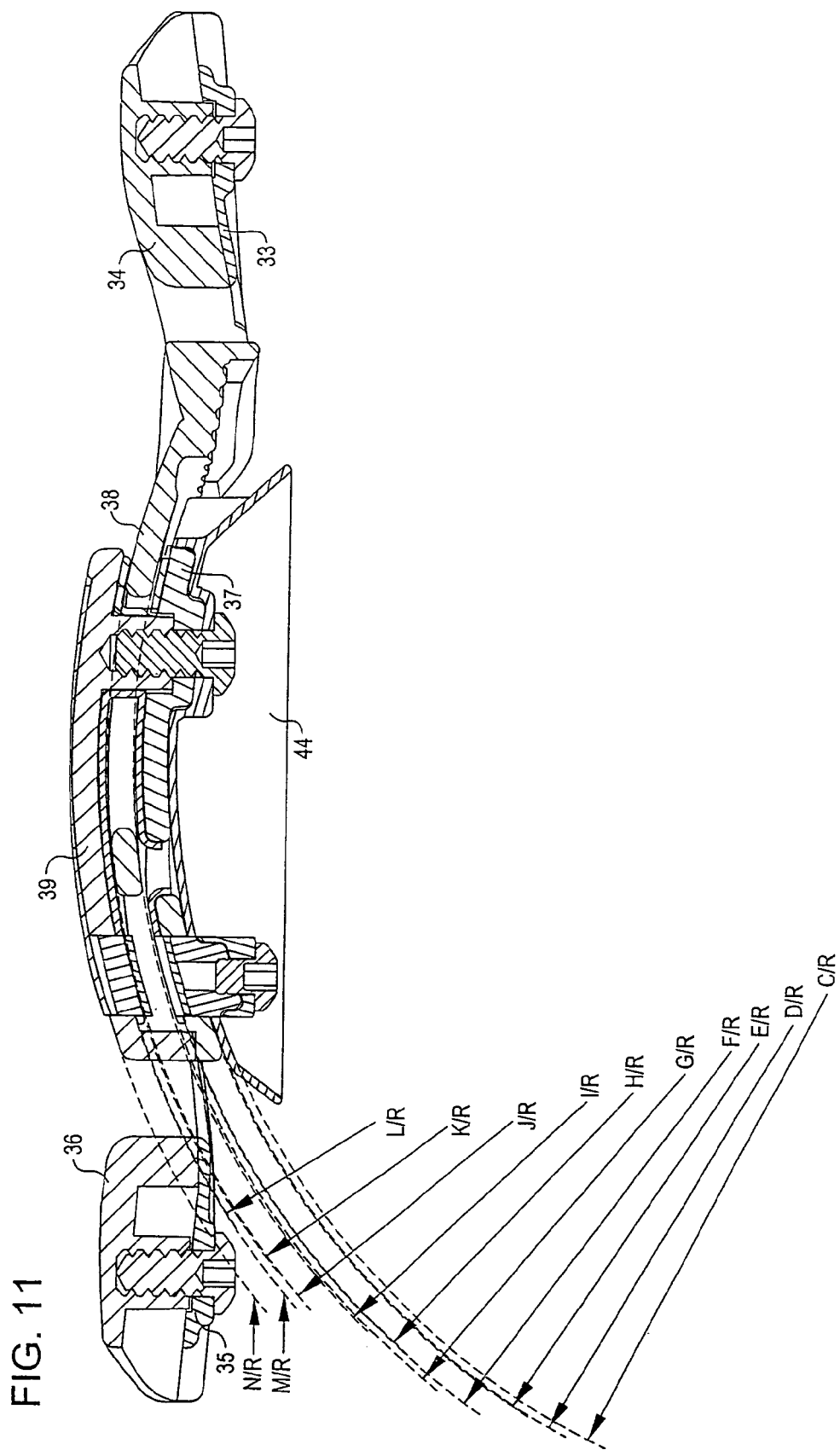

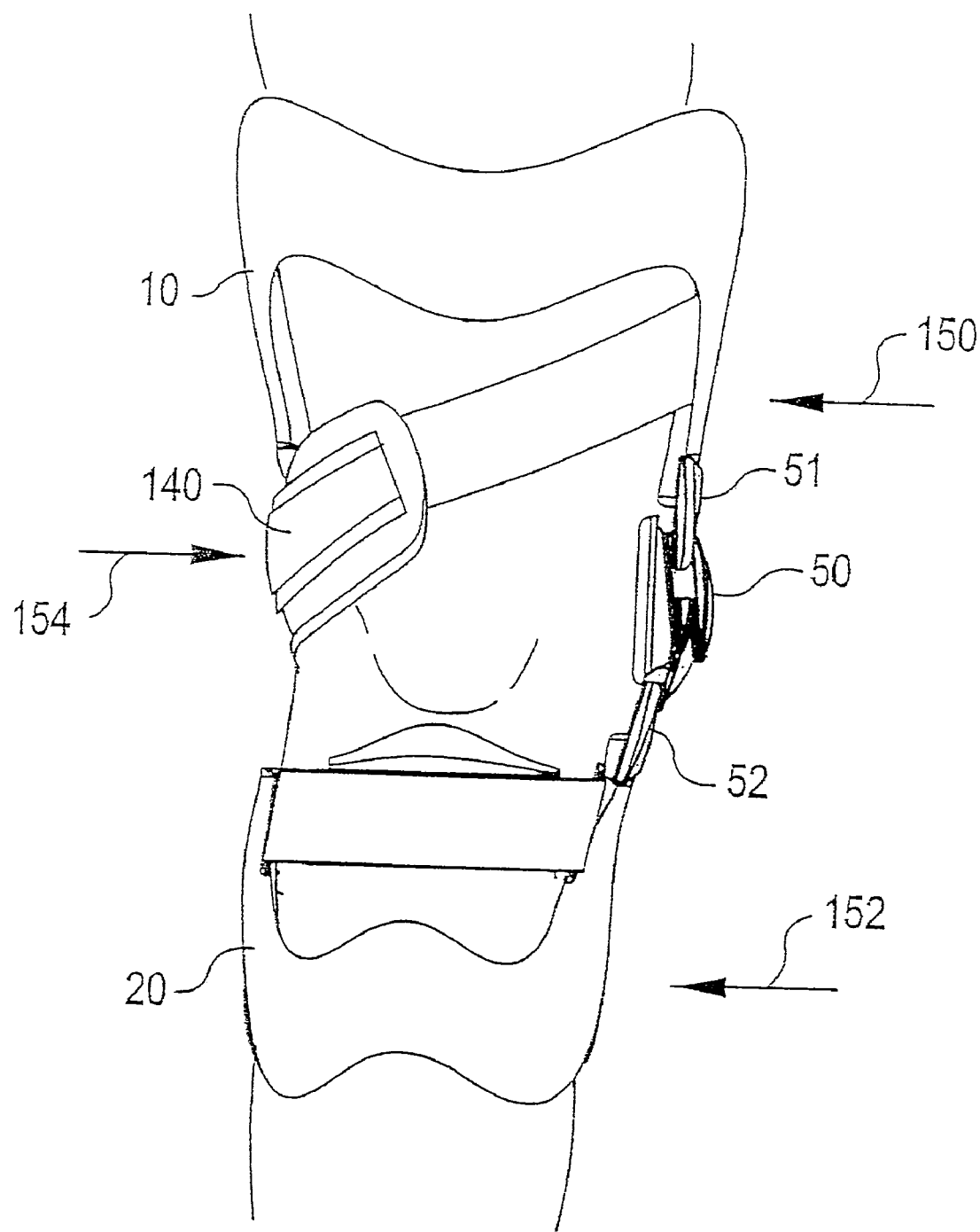

ND ORTHOPEDIC
ANATOMICALLY DESIGNED ORTHOPEDIC KNEE BRACE

CROSS REFERENCES TO RELATED APPLICATIONS

This application is a continuation-in-part of U.S. patent application Ser. No. 10/187,008, filed Jun. 28, 2002 now U.S. Pat. No. 6,969,364, incorporated herein by reference. This application also claims the priority benefit of U.S. Provisional Application No. 60/417,819, filed Oct. 11, 2002, incorporated herein by reference.

FIELD OF THE INVENTION

The present invention relates to improved orthopedic devices for treating or preventing knee injury or disease.

BACKGROUND

Knee brace devices are designed to provide control over movement of the human knee following injury, during recuperation from injury, and to provide protection of the knee to prevent, treat, or aid in the healing of, knee injury or disease. Existing orthopedic knee braces do not take into account a complete understanding of the anatomy of the knee joint and particularly knee kinematics. For these reasons, existing knee braces fail to accommodate and adequately control a full range of motion of the knee. These deficiencies in existing knee brace devices limit their usefulness and impair the ability of the knee joint to heal during recuperation following injury or disease.

The human knee joint is formed by the distal end of the femur, particularly the medial and lateral femoral condyles, and the proximal end of the tibia, particularly the respective medial and lateral tibial plateaus. The condyles of the femur articulate upon the tibial plateaus. The medial and lateral condyles are not symmetric in size or shape, with respect to one another, nor are the articular surfaces of the corresponding tibial plateaus.

The knee joint is a complex hinge mechanism with many motions in multiple planes taking place simultaneously, with six degrees of freedom. Flexion and extension take place in the sagittal plane. During normal human locomotion the knee ranges from zero degrees, which is defined as full extension (straight leg), to an average of about 60 degrees of flexion (bent knee position). When a person increases activity, for example jogging or sprinting, knee range of motion increases somewhat relative to the person's velocity. The natural roll and glide of the femur on the tibial plateau occurs in an anterior and posterior motion within the sagittal plane. As the femur rolls back on the tibia during flexion it also glides. Since the medial and lateral condyles are essentially spherical and have different radii, they rotate and glide at a different rate. The differential rollback creates a complex asymmetric motion to the knee.

Further motion linked to the knee flexion and extension occurs in the frontal plane. As the knee flexes, the ankle moves toward the midline of the body to create adduction (or varus). As the knee extends, the ankle moves away from the midline of the body to create abduction (or valgus). Simultaneous motion also occurs in the transverse plane. The tibia exhibits internal and external rotation with respect to the femur. As the knee flexes the tibia internally rotates with respect to the femur. As the knee extends the tibia externally rotates. This phenomenon is known as "the screw home mechanism." The screw home motion is a result of ligament and other soft tissue tension, as well as the articular geometry and relationship between the medial and lateral femoral condyles with the respective tibial plateaus. As the knee flexes and extends, the tibia further exhibits proximal/distal motion and medial/lateral motion with respect to the femur.

Injury to the knee, such as major ligament injury, is a major factor leading to knee osteoarthritis or degenerative joint disease. Injury to the knee disrupts the dynamic coupling of the various independent but simultaneous motions. Interference with the natural anatomical motions of the knee results in incongruence between the femoral condyles and their respective tibial plateaus. This incongruence creates instability of the knee as well as excessive loading of the articular surfaces of the joint, leading to knee osteoarthritis.

The knee is the most commonly affected weight-bearing joint, and varus deformity is a common malalignment of the knee associated with osteoarthritis. Nonoperative measures that have been shown to be effective for the treatment of osteoarthritis of the knee include, education, telephone contact, weight loss, a walking program, a muscle-strengthening program, and analgesics to control pain. Intra-articular injections of hyaluronic acid, orgotein, and glucocorticosteroids seem to provide short-term relief, but they must be repeated frequently.

There are a number of systemic factors which increase vulnerability to joint damage, most notably age (esp. female gender after age 50), genetic susceptibility and obesity. A variety of other systemic factors, such as nutrition and physical activity, also play a large role. Those systemic factors that increase systemic vulnerability to joint damage either work by or contribute to intrinsic joint vulnerability.

Local factors and the local joint organ environment are anatomic and physiologic aspects of articular and periarticular tissues, especially emphasizing those elements that influence load distribution. These factors are specific to the joint site. The local environment tends to be neglected in current therapy, except exercise, and is a relatively untapped target for disease modification. Improving the local environment may alter the course of the disease. At minimum, it can strengthen the effect of pharmacologic agents.

In normal knees, biomechanical forces create an adduction moment during stance which results in 60 to 80 percent of the load going to the medial compartment. This biomechanical phenomenon may explain the greater frequency of medial versus lateral tibial femoral osteoarthritis. The adduction moment increases with the increasing magnitude of varus alignment, which contributes to medial osteoarthritis progression. Thus, varus alignment increases the adduction moment, which in turn increases medial knee compartment load. Conservative approaches that unload the compartments stressed by malalignment include bracing and wedge insole foot orthoses.

Orthopedic devices that have been evaluated for the treatment of varus gonarthrosis include wedged insoles and braces. Two main types of braces, sleeves and unloading braces, are available. Each is used in an attempt to decrease loads through the tibiofemoral joint. As the sleeve provides little mechanical support to the knee, it is thought that the feelings of improved stability and reduced pain are largely due to an improvement in joint proprioception. Kirkley, et al., *J. Bone and Joint Surgery*, 81: 539–547, 1999.

Osteoarthritis is a common disorder affecting synovial joints, with structural changes of osteoarthritis present in approximately half of the adult population. Osteoarthritis of the knee often results from joint overuse and or joint injury leading to premature breakdown of articular and lunar cartilage within the femoral-tibial compartment of the knee.

Roughly seven million people are currently diagnosed with knee osteoarthritis, and this number is expected to double by the year 2020. It is expected that 18 percent of the U.S. population will have some form of arthritis and commensurate increase in costs for their care by the year 2020. Osteoarthritis knee braces attempt to create an opposing abduction moment (in the case of varus knee osteoarthritis), to unload the diseased compartment of the knee. Although there are numerous knee braces commercially available. For example, the Unloader® (Generation II USA) has been tested in randomized clinical trials and proven effective. The Unloader® brace works by creating a force which reduces the load on the symptomatic compartment by a three-point force system and a single upright hinge. The angle of the hinge is adjustable, and increases the abduction moment, to further decrease the load to the medial compartment. A 'dynamic force strap' produces the contralateral third point of force. See *Knee Osteoarthritis: A Biomechanical Approach to the Pathogenesis and Treatment,* Clinical Symposium at the American College of Rheumatology (ACR) and the Association of Rheumatology Health Professionals (ARHP) Annual Scientific Meeting, Nov. 11–15, 2001 in San Francisco, Calif.

Knee braces have been designed to protect and provide control for the human knee. Most designs ignore the three dimensional asymmetric motion critical to the healthy preservation of the anatomical knee joint, controlling motion in a single, sagittal plane. The rigidity found in these types of braces provides good protection from external impact to the knee, but as a result of the limited single plane motion, do not protect or preserve the articular surfaces of the joint.

Examples of previously described knee braces include devices for stabilizing a knee joint that provide a hinge mechanism with a cam follower and a cam slot. U.S. Pat. No. 4,723,539. The hinge allows the knee joint to move in a forward to rearward motion only within the sagittal plane during flexion and extension of the knee joint while in the appliance. The hinge mechanism of the knee brace does not control any other planes of motion of the knee joint.

Other known knee brace devices provide a hinge for use in an orthopedic knee brace, wherein the hinge has linking and pivot members proposed to simulate movement of the tibia in relation to the femur. U.S. Pat. No. 5,230,697. In this type of hinge mechanism, the pivot point in the hinge varies or changes during rotational movement. Principal movement of the knee within the knee brace occurs within the sagittal plane. The hinge mechanism reportedly controls movement within a single plane, but fails to control other planes of motion of the knee joint.

Other examples of hinges for use in an orthopedic knee brace attempt to provide for movement of the knee joint in three dimensions. These knee braces may allow movement in four of the six degrees of freedom, and potentially five of the six degrees of rotational freedom, of the anatomical knee joint. U.S. Pat. No. 5,792,086 and U.S. Pat. No. 5,107,824. However, in the first of these designs the proximal distal motion of the tibia in relation to the femur is accommodated by a sliding portion of the tibial section of the knee brace, not by the hinge mechanism. The sliding portion adds considerable bulk to the knee brace, which may be undesirable to certain wearers of knee orthoses. Another limitation of this design is that the hinges and the entire knee brace are flexible, not rigid. The plasticity of all components is necessary to prevent binding and restriction during asymmetric motion of the hinges. When hinges with three dimensional geometry in a pin-in-slot pattern of the prior design are used in a rigid knee brace, the prior art knee brace tends to bind resulting in excessive component wear.

The knee braces of prior design may fail under certain conditions of use. The knee braces of prior design do not offer protection to the wearer's knee and leg from outside impact. The knee braces of the prior design may fail under load. The slot and pins may wear substantially due to friction, placing a burden on the knee brace and the wearer, and limiting the useful life of the product.

In the second design, the knee brace may lack the rigidity necessary to properly brace the knee joint under certain conditions. In one important aspect, the hinges of the knee brace are not rigidly fixed relative to one another. The medial and lateral hinges exist independently in medial and lateral cuffs, respectively, and are held together by flexible straps. This flexibility allows movement of the hinges and or the thigh and calf cuffs to prevent the binding that takes place as a result of the mechanical hinge asymmetry. This knee brace therefore does not brace the knee joint in six degrees of freedom of movement.

Additional knee braces are provided in a variety of design variations and are known in the art as produced by such makers as Omni™, Donjoy™, Orthotech™, BREG™, Lenox Hill™, Townsend™, and CTI™. Each of these alternative knee brace designs has notable deficiencies in accordance with one or more aspects of the foregoing discussion. None of these additional devices properly brace the knee joint in six degrees of freedom of movement.

In view of the foregoing, a compelling need exists in the art for an orthopedic knee brace that will more accurately track anatomical motion of the knee and provide an improved construction as required for sufficient external support and protection of the knee. A related need exists for an improved knee brace adapted to treat or prevent advancing symptoms of osteoarthritis of the knee.

SUMMARY OF THE INVENTION

The present invention fulfills the foregoing needs and satisfies additional objects and advantages by providing a novel and effective orthopedic knee brace. The orthopedic knee brace in accordance with the present invention is used for treatment and rehabilitation following surgery to the knee, protection for a surgically repaired knee, and protection for an uninjured knee, among other applications. The orthopedic knee brace is useful for most types of surgical repairs to the knee and for prevention of many types of damage to the knee.

The orthopedic knee brace in accordance with the present invention provides an apparatus for accurately prescribing the anatomical motion of the human knee. The orthopedic knee brace prescribes movement of the knee joint in three dimensions and in six degrees of freedom simultaneously. The orthopedic knee brace actively prescribes asymmetric three-dimensional anatomic motion between a femur and a tibia during flexion and extension of a wearer's leg. The orthopedic knee brace actively prescribes flexion and extension, abduction and adduction, internal/external rotation, anterior/posterior translation, medial/lateral translation and proximal/distal translation between a femur and a tibia of a wearer's leg. The orthopedic knee brace permits natural movement of the knee which allows improved treatment and rehabilitation of a damaged knee or protection for a surgically repaired or an uninjured knee.

The orthopedic knee brace in accordance with the present invention comprises a thigh engaging member and a calf engaging member that are connected to one or more medial and/or lateral hinge(s). In certain embodiments of the invention directed toward treatment or prevention of knee injury, a two hinge design is employed. In these embodiments, the thigh engaging member and the calf engaging member are substantially rigid. The thigh engaging member securely engages the wearer's thigh and is rigidly connected to a medial hinge and a lateral hinge. The connections between the thigh and calf engaging members and the medial and lateral hinges may comprise medial or lateral hinge extensions that allow the knee brace to actively prescribe asymmetric three-dimensional anatomic motion between a femur and a tibia during flexion and extension of a wearer's leg.

In various embodiments of the invention, the connections between the thigh and calf engaging members and the medial and lateral hinges are substantially rigid. In alternate embodiments the connections are semi-rigid or flexible. The connections between the thigh and calf engaging members and the medial or lateral hinge by way of the medial or lateral hinge extensions further provide the ability of the hinge mechanisms to actively prescribe motion of the knee in six degrees of freedom, three rotational degrees and three translational degrees. The connections between the thigh and calf engaging members and the hinge mechanism provide the ability of the orthopedic knee brace in accordance with the present invention to actively prescribe flexion and extension, abduction and adduction, internal/external rotation, anterior/posterior translation, medial/lateral translation and proximal/distal translation between a femur and a tibia of a wearer's leg.

In additional embodiments of the invention, a modified, single-hinged knee brace is provided for treatment or prevention of symptoms of osteoarthritis. The orthopedic knee brace in accordance with this embodiment of the invention is particularly effective for treatment and relief of symptoms of unicompartmental osteoarthritis of the knee. The orthopedic knee brace adapted for this use includes a unilateral, anatomical bracing hinge and exerts a counter-rotational force on the tibia while exerting a dynamic stabilizing force to the medial condyle or the lateral condyle of the wearer's knee for treatment and relief of symptoms of unicompartmental osteoarthritis of the knee.

In more detailed embodiments, the orthopedic knee brace modified for treatment or prevention of osteoarthritis of the knee prescribes asymmetric three-dimensional anatomic motion in six degrees of freedom between a femur and a tibia during flexion and extension of a wearer's leg. In one embodiment, the unilateral hinge of the orthopedic knee brace is lateral to the wearer's knee. In an alternative embodiment, the unilateral hinge of the orthopedic knee brace is medial to the wearer's knee. As in other embodiments, a thigh engaging member and a calf engaging member are interconnected via a hinge. When the brace employs a medial hinge, it functions to relieve unicompartmental osteoarthritis affecting the medial condyle of a wearer's knee. Alternatively, when the brace comprises a lateral hinge it serves to relieve unicompartmental osteoarthritis affecting the lateral condyle of a wearer's knee. The thigh engaging member and the calf engaging member may be substantially rigid, or may be flexible. The thigh engaging member securely engages the wearer's thigh and is connected to the hinge. The calf engaging member securely engages the wearer's calf and is likewise connected to the hinge.

BRIEF DESCRIPTION OF THE DRAWINGS

FIG. 5 is an exploded isometric view of the medial hinge.

FIG. 11 is a cross sectional view of the medial hinge.

FIG. 25 is a front perspective view of an anatomically designed unilateral hinge orthopedic knee brace for treatment and prevention of osteoarthritis in accordance with the present invention on a wearer's leg.

DETAILED DESCRIPTION OF THE INVENTION

Figure 1:
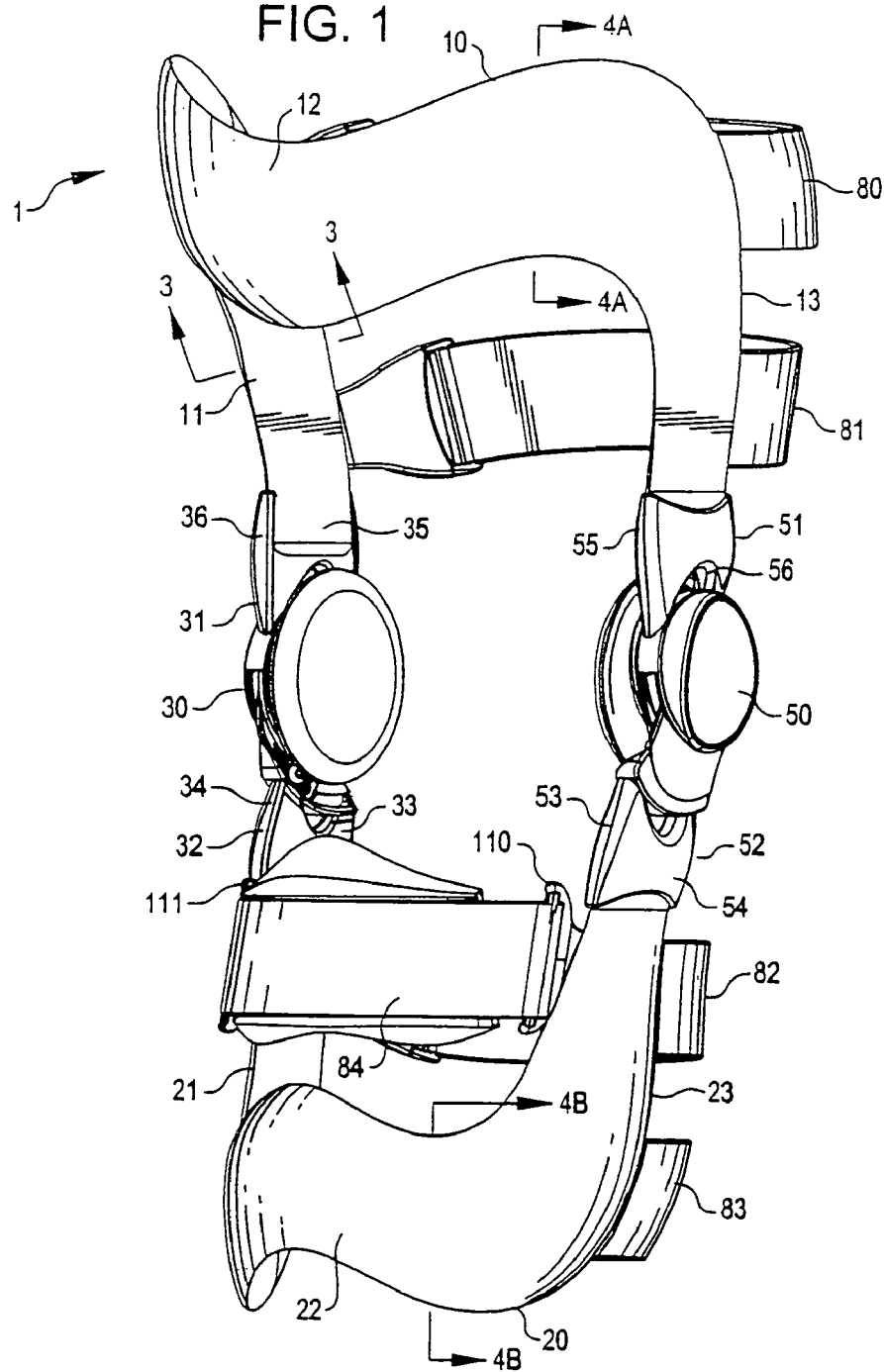
FIG. 1 is a front perspective view of an anatomically designed orthopedic knee brace in accordance with the present invention.

The orthopedic knee brace in accordance with the present invention provides an apparatus for accurately prescribing the anatomical motion of the human knee. Anatomical tracking, when used with bracing, protects the knee and reduces stress on the anatomical parts of the knee, particularly the ligaments and the articular surfaces.

The orthopedic knee brace in accordance with the present invention prescribes movement of the knee joint in three dimensions and in six degrees of freedom simultaneously. The orthopedic knee brace actively prescribes asymmetric three-dimensional anatomic motion between a femur and a tibia during flexion and extension of a wearer's leg. The orthopedic knee brace actively prescribes flexion and extension, abduction and adduction, internal/external rotation, anterior/posterior translation, medial/lateral translation and proximal/distal translation between a femur and a tibia of a wearer's leg. The orthopedic knee brace permits natural movement of the knee which allows improved treatment and rehabilitation of a damaged knee or protection for a surgically repaired or an uninjured knee.

For treatment and prevention of knee injuries, and to aid in healing and protection of the knee following surgery, an orthopedic knee brace of the invention comprises a thigh engaging member and a calf engaging member that are connected to medial and lateral hinges. The thigh engaging member and the calf engaging member are typically rigid or substantially rigid. The thigh engaging member securely engages the wearer's thigh and is rigidly connected to the medial hinge and lateral hinge. The calf engaging member securely engages the wearer's calf and is rigidly connected to the medial hinge and lateral hinge. In exemplary embodiments of the invention, the thigh engaging member comprises a medial portion, a lateral portion and an anterior portion. Likewise, an exemplary calf engaging member has a medial portion, a lateral portion and an anterior portion.

Typically, the thigh and calf engaging members are each rigidly connected to the medial and lateral hinges by medial and lateral hinge extensions. This construction facilitates the function of the brace to actively prescribe asymmetric three-dimensional anatomic motion between a femur and a tibia during flexion and extension of a wearer's leg. The rigid connections between the thigh and calf engaging members and the medial and lateral hinge extensions further provide the ability of the hinge mechanisms to actively prescribe motion of the knee in six degrees of freedom, three rotational degrees and three translational degrees. The rigid connections between the thigh and calf engaging members and the hinge mechanisms further provide the ability of the hinge mechanism to actively prescribe motion of the knee in six degrees of freedom, three rotational degrees and three translational degrees. The connections between the thigh and calf engaging members and the hinge mechanism provide the ability of the orthopedic knee brace in accordance with the present invention to actively prescribe flexion and extension, abduction and adduction, internal/external rotation, anterior/posterior translation, medial/lateral translation and proximal/distal translation between a femur and a tibia of a wearer's leg.

Within exemplary embodiments of the invention, the lateral hinge is positioned lateral to the wearer's knee and the medial hinge is positioned medial to the wearer's knee. The lateral hinge has an upper lateral hinge linkage for connecting the hinge to the lateral portion of the thigh engaging member and a lower lateral hinge linkage for connecting the hinge to the lateral portion of the calf engaging member. The medial hinge has an upper medial hinge linkage for connecting the hinge to the medial portion of the thigh engaging member and a lower medial hinge linkage for connecting the hinge to the medial portion of the calf engaging member. The thigh engaging member is substantially rigid and forms rigid connections between the thigh engaging member and the upper medial hinge linkage and between the thigh engaging member and the upper lateral hinge linkage. The calf engaging member is substantially rigid and forms rigid connections between the calf engaging member and the lower medial hinge linkage and between the calf engaging member and the lower lateral hinge linkage.

The rigidity of the components and connections between components of the orthopedic knee brace in accordance with the present invention is determined, for example, by resistance to compression of the knee brace in a medial-lateral direction. Rigidity of the orthopedic knee brace may be determined by forcing the medial hinge toward the lateral hinge a distance of 0.5 inches. The orthopedic knee brace is rigid or substantially rigid if compression of the knee brace by 0.5 inches in the medial lateral direction requires, in one embodiment, applying a force of approximately 15 pounds or greater, in another embodiment, approximately 25 pounds or greater; and in another embodiment, approximately 30 pounds or greater. In one exemplary embodiment, the orthopedic knee brace is determined to be rigid or substantially rigid if compression of the knee brace by 0.5 inches in the medial lateral direction requires applying a force of between approximately 25 pounds and approximately 35 pounds.

In more detailed aspects of the invention, the orthopedic knee brace comprises a lateral and/or medial hinge(s) having a plurality of parallel, concentric shells in the shape of a segment of a sphere. The shells have a plurality of cam follower pins and a plurality of cam slots. A side edge of the cam slot is parallel to a side of the cam follower pin. The cam follower pins are shaped to track the path of the cam slots from full flexion to full extension and prevent wear and binding of the lateral and medial hinges upon extended use by the wearer.

An extension stop member is located on the inner shell on the lateral and/or medial hinge(s). The extension stop member limits the movement of the orthopedic knee brace during flexion and extension of a wearer's leg. The extension stop member thereby prevents over-flexion or over-extension of the wearer's leg while the orthopedic knee brace is worn. The inner shell of the hinge has a catch which contacts the extension stop on the extension stop member. Contact between the catch and the extension stop limits extension of the tibia relative to the femur of a wearer's leg when the leg is secured by the thigh engaging member and calf engaging member of the orthopedic knee brace. The extension stop member is typically adjustable from a setting of about 0 degrees to 20 degrees flexion in five degree increments, for example by loosening a set screw, moving the extension stop, and retightening the set screw. These positional adjustments control the limits of extension of the wearer's leg from about 0 degrees flexion (full extension) to about 20 degrees flexion (partially limited extension). Zero degrees flexion to 20 degrees flexion corresponds to a minimum angle of flexion of the wearer's leg while in the orthopedic knee brace in accordance with the present invention. In further embodiments, the extension stop member may limit extension of the wearer's leg to 30 degrees flexion, or alternatively, to 40 degrees flexion.

In a further detailed aspect, the plurality of cam follower pins engage the plurality of cam slots to rotatably engage the parallel, concentric, spherical shells. A side of the cam follower pin is shaped to track a path parallel to a side of the cam slot. In a further detailed embodiment, the side of the cam follower pin at a point closest to the cam slot is parallel to the side of the cam slot throughout the range of motion from flexion to extension of the knee brace.

In a further detailed aspect, a side of the cam follower pin at a point closest to the cam slot, shaped to track a path parallel to a side of the cam slot, is at an angle to a radial axis of the spherical shell. In one aspect, the cam follower pin is essentially a cylinder, in which case a cross section of the cam follower pin describes a circle. In an alternate aspect, the cam follower pin is not cylindrical, in which case a cross section of the cam follower pin describes an ellipse or other closed curved structure or closed curve plus straight-sided structure. In an alternate aspect, the cam follower pin is multisided, in which case a cross section of the cam follower pin describes a polygon. In a further detailed embodiment, the angle between the side edge of the cam follower pin, shaped to track a path parallel to a side of the cam slot, and the radial axis of the spherical shell of the hinge is between approximately 0 and 45 degrees. In another embodiment the angle is between approximately 10 and 35 degrees. In another embodiment, the angle is between approximately 20 and 25 degrees. The cam follower pins are typically shaped to track the path of the cam slots from full flexion to full extension and prevent wear and binding of the lateral and medial hinges upon extended use by the wearer.

In other aspects of the invention, an anatomical bracing hinge is provided for use in an orthopedic knee brace. The anatomical bracing hinge provides one or two hinge members selected from a medial hinge and a lateral hinge. The medial hinge comprises a first shell, a second shell, and a third shell in the shape of a segment of a sphere. The first and third shells are concentric and fastened parallel to each other to form a first opening. The first and third shells are fastened to one of a medial portion of a thigh engaging member and a calf engaging member, and the second shell is fastened to the other of the medial portion of the thigh engaging member and the calf engaging member. The second shell is designed to be inserted into the first opening. The second shell is concentric and parallel to the first and third shells. The first and third shells are rotatably engaged to the second shell by a plurality of cam follower pins engaging a plurality of cam slots. In two hinge brace designs, the lateral hinge comprises a fourth shell, a fifth shell, and a sixth shell in the shape of a segment of a sphere. The fourth and sixth shells are concentric and fastened parallel to each other to form a second opening. The fourth and sixth shells are fastened to one of a lateral portion of a thigh engaging member and a calf engaging member, and the fifth shell is fastened to the other of the lateral portion of the thigh engaging member and the calf engaging member. The fifth shell is designed to be inserted into the second opening. The fifth shell is concentric and parallel to the fourth and sixth shells. The fourth and sixth shells are rotatably engaged to the fifth shell by a plurality of cam follower pins engaging a plurality of cam slots. The medial and lateral hinges of the anatomical bracing hinge actively prescribe asymmetric three-dimensional anatomic motion between a femur and a tibia during flexion and extension of a wearer's leg.

In related aspects, the anatomical bracing hinge for use in an orthopedic knee brace actively prescribes asymmetric three-dimensional anatomic motion between a femur and a tibia during flexion and extension of a wearer's leg. The medial and/or lateral hinge(s) function within a knee brace as described herein to actively prescribe flexion and extension, abduction and adduction, internal/external rotation, anterior/posterior translation, medial/lateral translation, and proximal/distal translation between a femur and a tibia of a wearer's leg.

In additional aspects, the anatomical bracing hinge in accordance with the present invention may comprise cam follower pins with a side edge of the cam follower pin at an angle to a radial axis of the spherical shell. The angle of a side of the cam slot is parallel to the side edge of the cam follower pin. The cam follower pins are shaped to track the path of the cam slots from full flexion to full extension and prevent wear and binding of the lateral and medial hinges.

In other detailed aspects, the plurality of cam follower pins engage the plurality of cam slots to rotatably engage the parallel, concentric, spherical shells to form the anatomical bracing hinge. A side edge of the cam follower pin is shaped to track a path parallel to a side of said cam slot. In related aspects, the side edge of the cam follower pin at a point closest to the cam slot may be parallel to the side of the cam slot throughout the range of motion from flexion to extension of the knee brace.

In other embodiments of the invention, a method of constructing an orthopedic knee brace in accordance comprises constructing a thigh engaging member and a calf engaging member as described herein from a rigid material. A lateral hinge and a medial hinge as described herein is/are connected to the thigh and calf engaging members at a fixed distance along an instantaneous axis of rotation of the wearer's knee. The distance between the lateral hinge and the medial hinge is adjusted to fit a pin/slot geometry whereby the knee brace prescribes asymmetric three-dimensional anatomic motion in six degrees of freedom by actively prescribing flexion and extension, abduction and adduction, internal/external rotation, anterior/posterior translation, medial/lateral translation and proximal/distal translation between a femur and a tibia of a wearer's leg.

The orthopedic knee brace in accordance with the present invention actively prescribes medial lateral translation during flexion and extension of the orthopedic knee brace. In one embodiment, the range of medial lateral translation during flexion and extension of the orthopedic knee brace is from approximately 2 millimeters of medial translation to approximately 6 millimeters of lateral translation. In a further embodiment, the range of medial lateral translation is from approximately zero millimeters to approximately 6 millimeters of lateral translation. In a further embodiment, the range of medial lateral translation is from approximately zero millimeters to approximately 4 millimeters of lateral translation.

The orthopedic knee brace in accordance with the present invention actively prescribes anterior posterior translation during flexion and extension of the orthopedic knee brace. In one embodiment, the range of anterior posterior translation during flexion and extension of the orthopedic knee brace is from approximately zero millimeters to approximately 25 millimeters of anterior translation. In a further embodiment, the range of anterior posterior translation is from approximately zero millimeters to approximately 20 millimeters of anterior translation. In a further embodiment, the range of anterior posterior translation is from approximately 0 millimeters to approximately 16 millimeters of anterior translation.

The orthopedic knee brace in accordance with the present invention actively prescribes proximal distal translation during flexion and extension of the orthopedic knee brace. In one embodiment, the range of proximal distal translation during flexion and extension of the orthopedic knee brace is from approximately zero millimeters to approximately 12 millimeters of proximal translation. In a further embodiment, the range of proximal distal translation is from approximately zero millimeters to approximately 5 millimeters of proximal translation. In a further embodiment, the range of proximal distal translation is from approximately 0 millimeters to approximately 9 millimeters of proximal translation.

The orthopedic knee brace in accordance with the present invention actively prescribes internal external rotation during flexion and extension of the orthopedic knee brace. In one embodiment, the range of internal external rotation during flexion and extension of the orthopedic knee brace is from approximately 0 degrees to approximately 25 degrees of internal rotation. In a further embodiment, the range of internal external rotation is from approximately 0 degrees to approximately 5 degrees of internal rotation. In a further embodiment, the range of internal external rotation is from approximately 0 degrees to approximately 10 degrees of internal rotation.

The orthopedic knee brace in accordance with the present invention actively prescribes adduction-abduction (varus-valgus) rotation during flexion and extension of the orthopedic knee brace. In one embodiment, the range of adduction-abduction (varus-valgus) rotation during flexion and extension of the orthopedic knee brace is from approximately 0 degrees to approximately 10 degrees of adduction rotation. In a further embodiment, the range of adduction-abduction is from approximately 0 degrees to approximately 2 degrees of adduction rotation. In a further embodiment, the range of adduction-abduction rotation is from approximately 0 degrees to approximately 5 degrees of adduction rotation.

The concentric, parallel spherical shells of the lateral hinge have radii that differ from the radii of the concentric, parallel, spherical shells of the medial hinge. In one embodiment, the values of the radii of the first, second and third shells of the lateral hinge may range from approximately 2.5 inches to approximately 3.5 inches within the scope of the anatomically designed orthopedic knee brace. In a further embodiment, the values of the radii of the shells of the lateral hinge may range from approximately 2.7 inches to approximately 3.4 inches. In a further embodiment, the values of the radii of the shells of the lateral hinge may range from approximately 2.9 inches to approximately 3.3 inches. In one embodiment, the values of the radii of the fourth, fifth and sixth shells of the medial hinge may range from approximately 1.5 inches to approximately 2.5 inches within the scope of the anatomically designed orthopedic knee brace. In a further embodiment the values of the radii of the shells of the medial hinge may range from approximately 1.7 inches to approximately 2.4 inches. In a further embodiment, the values of the radii of the shells of the medial hinge may range from approximately 1.8 inches to approximately 2.3 inches. The radii of the spherical shells and the pin/slot geometry of medial and lateral hinges provide an orthopedic knee brace that actively prescribe asymmetric three-dimensional anatomic motion between a femur and a tibia during flexion and extension of a wearer's leg.

In another embodiment, an orthopedic knee brace for controlling movement of a wearer's knee comprises a thigh engaging means and a calf engaging means. The thigh engaging means may be a thigh engaging member. The calf engaging means may be a calf engaging member. The orthopedic knee brace in accordance with the present invention further comprises a first interengaging control means for rotatably connecting said thigh engaging means to said calf engaging means and a second interengaging control means for rotatably connecting said thigh engaging means to said calf engaging means. The first interengaging control means and the second interengaging control means may be a lateral hinge and a medial hinge rotatably connecting the thigh engaging means to the calf engaging means. The thigh engaging means is typically substantially rigid and forms rigid connections between the thigh engaging means and the first interengaging control means and between the thigh engaging means and the second interengaging control means. The calf engaging means is substantially rigid and forms rigid connections between the calf engaging means and the first interengaging control means and between the calf engaging means and the second interengaging control means. The rigid connections facilitate the function of the orthopedic knee brace to actively prescribe asymmetric three-dimensional anatomic motion between a femur and a tibia during flexion and extension of a wearer's leg. The orthopedic knee brace actively prescribes flexion and extension, abduction and adduction, internal/external rotation, anterior/posterior translation, medial/lateral translation and proximal/distal translation between a femur and a tibia of a wearer's leg.

FIG. 1 illustrates an exemplary embodiment of an anatomically designed orthopedic knee brace 1 in accordance with the present invention. In this example, only the orthopedic knee brace and hinge for the right leg are described. It is to be understood that the orthopedic knee brace for the left leg will be a mirror image of that described herein. The orthopedic knee brace shows a substantially rigid design of the brace and a rigid connection of the thigh engaging member 10 and the calf engaging member 20 to the lateral hinge 30 and medial hinge 50. The thigh engaging member and the calf engaging member will often comprise a solid piece molded and formed to the contours of the wearer's thigh and calf. The thigh engaging member typically has lateral 11, anterior 12, and medial 13 portions, respectively. The calf engaging member will typically have lateral 21, anterior 22, and medial 23 portions, respectively. The anterior portions of the thigh and calf engaging members will typically be undulated to effectively and comfortably engage and control the soft tissue of the thigh or calf.

The thigh engaging member and the calf engaging member are typically rigid and may be constructed, for example, of reinforced fiber-filled thermoplastic resin or comparably rigid materials. The resin can be molded to provide a basic shape and later heated and formed to a desired shape, in this case, to conform to corresponding thigh and calf surfaces of a human leg.

As used herein, the term "rigid", "substantially rigid", and "rigidly connected" refers to an orthopedic knee brace, or one or more parts or interconnecting elements thereof, including hinge and hinge components, that serve to guide and restrain relative movement of a wearer's knee. The orthopedic knee brace or component(s) thereof possess a "rigid" construction as reflected by the ability of the knee brace to firmly hold the wearer's knee at any given position of the knee during flexion or extension of a wearer's leg, wherein the brace or subject component(s) provide greater stiffness or force resistance than exerted on the brace or subject component(s) by the than the wearer's knee at any given position of the knee within the brace during flexion or extension of the wearer's leg. As an alternate measure of rigidity, the orthopedic knee brace, or component(s) thereof possess a "rigid" construction in that the knee brace accurately, correctly, and actively prescribes asymmetric three-dimensional anatomic motion between a femur and a tibia during flexion and extension of a wearer's leg. Rigid construction of the brace and/or its component structures is also reflected by the functionality of the brace to accurately, correctly, and actively prescribe motion of the wearer's knee in six degrees of freedom, three rotational degrees and three translational degrees. The six degrees of freedom are flexion and extension, abduction and adduction, internal/external rotation, anterior/posterior translation, medial/lateral translation and proximal/distal translation between a femur and a tibia of a wearer's leg.

In exemplary embodiments, the orthopedic knee brace or a component or interconnecting element thereof is determined to be "rigid", "substantially rigid", or "rigidly connected" as measured by a lateral compression test that quantifies the rigidity of the knee brace. Rigidity in this context may be determined by the amount of force in pounds required to compress an orthopedic knee brace one half inch in the medial-lateral direction. As described in detail in Example 1 below, the lateral compression test may be conducted, for example, by clamping the knee brace at either the medial or lateral hinge element. A pneumatic press compresses the opposing hinge elements toward each other by 0.5 inches. The force required under load to compress the brace by 0.5 inches is determined. The force is measured in units of pounds. In one embodiment, the orthopedic knee brace is considered "rigid", "substantially rigid", or "rigidly connected" if the force required under load to compress the brace by 0.5 inches is 15 pounds or greater. In another embodiment, the force required is 25 pounds or greater. In a further embodiment, the force required is 30 pounds or greater. In one exemplary embodiment, the orthopedic knee brace or component or interconnecting element thereof is rigid or substantially rigid if the force required under load to compress the brace by 0.5 inches is between approximately 25 pounds and approximately 35 pounds. It is understood in the art that there may be alternative measures of rigidity of the orthopedic knee brace that will correlate with the functional and performance requirements specified herein.

In two-hinge brace designs of the invention, the lateral hinge 30 is attached to the lateral portion 11 of the thigh engaging member 10 by an upper lateral hinge linkage 31 and to the lateral portion 21 of the calf engaging member 20 by a lower lateral hinge linkage 32. The medial hinge 50 is attached to the medial portion 13 of the thigh engaging member 10 by an upper medial hinge linkage 51 and to the medial portion 23 of the calf engaging member 20 by a lower medial hinge linkage 52. The upper and lower hinge linkages are rigid and form a rigid connection to the lateral and medial portions of the thigh and calf engaging members.

The lateral hinge 30 and medial hinge 50 and the upper and lower hinge linkages may be made from a variety of materials that impart sufficient rigidity to the hinge construction, including various metals and composite materials such as graphite, plastic, or resin composites. In certain embodiments the linkages may be constructed from one or more metals, for example, die cast aluminum or machined wrought aluminum. The upper and lower hinge linkages are rigidly connected to the thigh engaging member and calf engaging member by a rigid connecting element, for example metal (e.g., stainless steel) or composite (e.g., graphite/resin) pins, bolts, screws, rivets, and like connectors.

In one exemplary embodiment, the upper lateral hinge linkage 31 has an inner spherical plate extension 35 and an outer spherical plate extension 36 that are attached to the lateral portion 11 of the thigh engaging member. The attachment forms a rigid linkage between the thigh engaging member 10 and the lateral hinge 30. Similarly, the upper medial hinge linkage 51 has an inner spherical plate extension 55 and an outer spherical plate extension 56 that are attached to the medial portion 13 of the thigh engaging member. The attachment forms a rigid linkage between the thigh engaging member 10 and the medial hinge 50.

The lower lateral hinge linkage 32 typically has a lateral retainer plate 33 and a center spherical plate extension 34 that are attached to the lateral portion 21 of the calf engaging member. The attachment forms a rigid linkage between the calf engaging member 20 and the lateral hinge 30. Similarly, the lower medial hinge linkage 52 has a medial retainer plate 53 and a center spherical plate extension 54 that are attached to the medial portion 23 of the calf engaging member. The attachment forms a rigid linkage between the calf engaging member 20 and the medial hinge 50.

Figure 2:
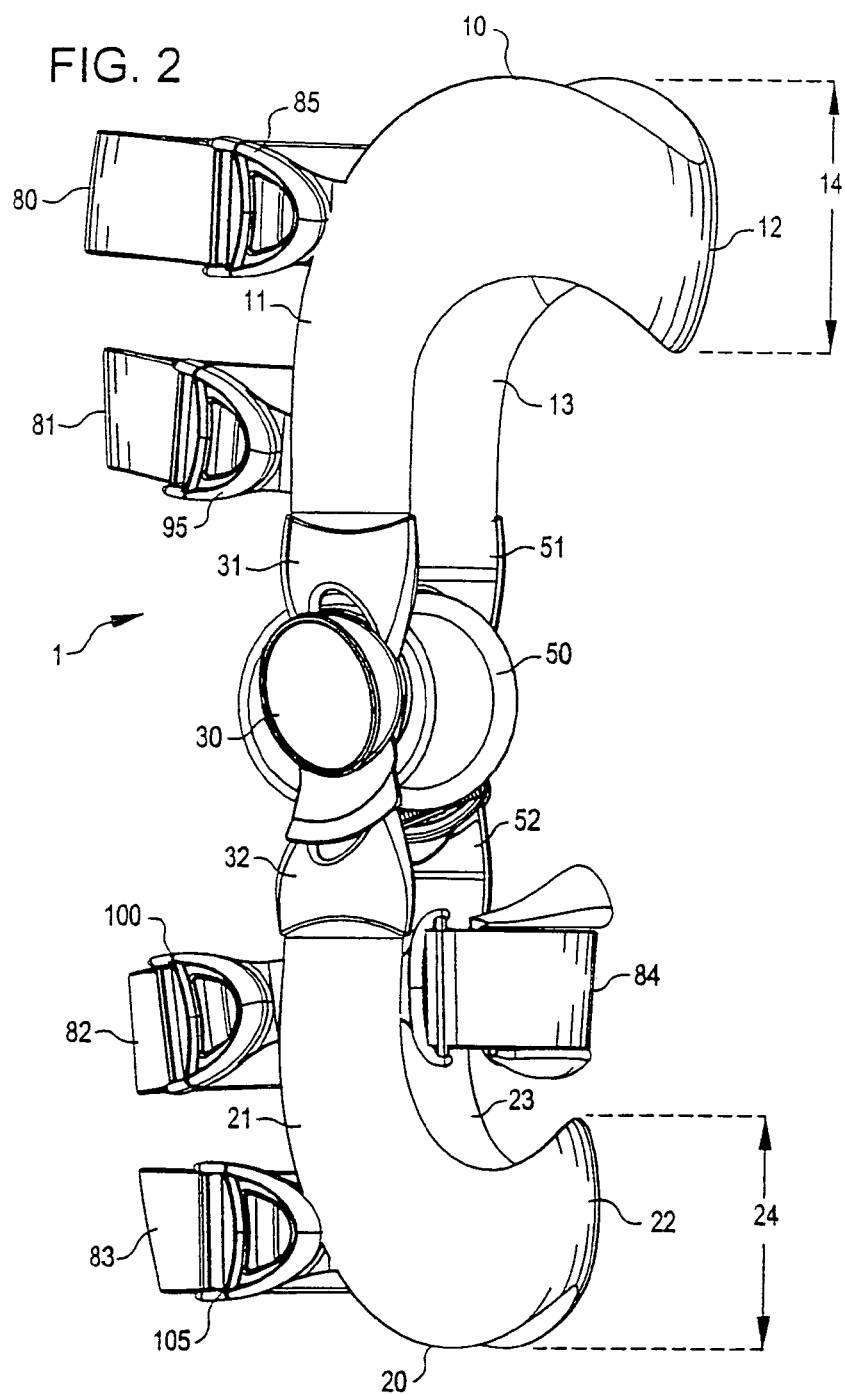
FIG. 2 is a side perspective view of the anatomically designed orthopedic knee brace.

FIG. 2 provides a side perspective view of one exemplary embodiment of an anatomically designed two-hinge orthopedic knee brace 1 of the invention. The brace features a substantially rigid design overall, particularly including a rigid interconnection of the thigh engaging member 10 and the calf engaging member 20 to the lateral hinge 30 and medial hinge 50. The thigh engaging member and the calf engaging member will often comprise a solid molded element formed to the contours of the wearer's thigh and calf as shown. The thigh engaging member typically has a lateral portion 11, an anterior portion 12, and a medial portion 13. The calf engaging member typically has a lateral portion 21, an anterior portion 22, and a medial portion 23. The anterior portions 12 and 22 of the thigh and calf engaging members are respectively shaped to securely and comfortably engage the soft tissue of the thigh and calf. The thigh engaging member and the calf engaging member are shaped to maximize the area of contact between the wearer's thigh and the thigh engaging member and between the wearer's calf and the calf engaging member. FIG. 2 shows the area 14 of the anterior portion of the thigh engaging member and the area 24 of the anterior portion of the calf engaging member that effectively cover the soft tissue area of the thigh and calf. Anterior portion 12 of the thigh engaging member has a marginal contour that curves from a proximal to a distal aspect of the thigh moving from the medial or lateral portion toward the center of the anterior portion of the thigh engaging member. Area 14 is maximized to effectively control movement of the femur by the orthopedic knee brace.

The contoured shape of the thigh engaging member accommodates muscle activity of the thigh during movement. The anterior portion 22 of the calf engaging member has a marginal contour that curves from a distal to a proximal aspect of the calf from the medial or lateral portion toward the center of the anterior portion of the calf engaging member. Area 24 is maximized to effectively control movement of the tibia by the orthopedic knee brace. The contoured shape of the calf engaging member accommodates muscle activity of the calf during movement. The shape of the medial, lateral, and anterior portions of the thigh engaging member and the calf engaging member of the anatomically designed orthopedic knee brace in accordance with the present invention effectively controls movement of the knee joint in six degrees of freedom, actively prescribing flexion and extension, abduction and adduction, internal/external rotation, anterior/posterior translation, medial/lateral translation and proximal/distal translation between a femur and a tibia of a wearer's leg.

The shape of the medial, lateral and anterior portions of the thigh engaging member and the calf engaging member may vary. For example, the shape of the anterior portion of the thigh engaging member and the calf member may have a deeper or shallower marginal curve in the proximal to distal aspect. The area 14 of the thigh engaging member or area 24 of the calf engaging member may be deeper or shallower. These and other variations in contour and design provide an anatomically designed orthopedic knee brace that more effectively controls movement of the knee joint and actively prescribes asymmetric three-dimensional anatomic motion between a femur and a tibia during flexion and extension of a wearer's leg in six degrees of freedom.

To securely hold the wearer's thigh in the orthopedic knee brace, the brace typically includes thigh attachment means 80, 81 in combination with or connected to the thigh engaging member 10. In exemplary embodiments, the thigh attachment means secure the undulated area 14 of the anterior portion 12, the lateral portion 11, and the medial portion 13 of the thigh engaging member 10 in close contact with the soft tissue area of the thigh. Calf attachment means 82, 83 securely hold the wearer's calf in the orthopedic brace. Calf attachment means 82, 83 and shin attachment means 84 in combination with the calf engaging member 20 will typically be provided to hold the undulated area 24 of the anterior portion 22 the lateral portion 21, and the medial portion 23 of the calf engaging member 20 securely against the soft tissue area of the calf. Thigh attachment means in combination with the thigh engaging member securely hold the femur of the wearer within the orthopedic knee brace. Calf attachment means in combination with the calf engaging member securely hold the tibia of the wearer within the orthopedic knee brace. These aspects of the invention contribute to effective control of movement of the knee joint and actively prescribe asymmetric three-dimensional anatomic motion between a femur and a tibia during flexion and extension of a wearer's leg in six degrees of freedom.

In certain embodiments the thigh attachment means, calf attachment means, and/or shin attachment means include flexible straps, for example straps secured against or connected to the thigh engaging member and/or calf engaging member by strap attachment elements. The strap attachment elements can be selected from a variety of suitable attachment devices, for example, threaded metal (e.g., brass inserts). In an exemplary construction, the metal inserts may be machined and cold pressed in or injection molded into the thigh engaging means and calf engaging means. The straps may be attached to the inside surface of the thigh engaging means and calf engaging means next to the wearer's leg. This configuration of the strap attachment elements allows clothing of the wearer to slide more easily over the thigh engaging means, thigh attachment means, calf engaging means, and calf attachment means.

Figure 3:
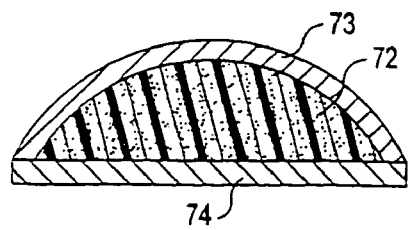
FIG. 3 is a cross section of the calf or thigh engaging member interface.

FIG. 3 provides a cross-sectional view (see arrows 3 in FIG. 1) of an exemplary thigh engaging member interface and exemplary calf engaging member interface of an orthopedic knee brace of the invention. The thigh engaging member interface and calf engaging member interface are typically constructed of a laminate combination. The laminate combination may be two or more different materials comprising a soft compressible material, a loop material, and a hydrophilic breathable material. A soft compressible type material 72 for accommodating pressure distribution may be bonded on one side to a loop material 73 for adhering the interface to the calf engaging member and may incorporate on the opposite side a hydrophilic, breathable material 74 that faces the skin of the user. The soft compressible material 72 will often be provided in a semi-elliptical shape to accommodate different leg shapes without causing localized pressure points to the wearer's leg. The thigh engaging member interface will often be of a shape that matches the inner width dimensions of the thigh engaging member anterior 12, medial 13, and lateral extension 11. The calf engaging member interface will generally be of a shape that matches the inner width dimensions of the calf engaging member anterior 22, medial 23, and lateral extension 21.

The soft compressible material 72 may be composed of, for example: foams or fabrics, polyurethane foam, EVA foam, polyester batting, or cotton fabric padding.

The hydrophilic, breathable material 74 may be composed of, for example: special knit or woven fabrics, suede leather, synthetic suede, spandex, polyester, brushed cotton, or other suitable fabric.

The loop material 73 may be composed of any loop and hook adherent material, for example VELCRO®.

Figure 4A:
FIGS. 4A and 4B are cross section views of the shape of the thigh engaging member and calf engaging member.
Figure 4B:

FIG. 4A provides a cross sectional view of the thigh engaging member 10 (see arrows 4A in FIG. 1). FIG. 4B provides a cross sectional view of the calf engaging member 20 (see arrows 4B in FIG. 1). The thigh engaging member and the calf engaging member may be constructed of any material that imparts suitable rigidity, for example metals, polymers, and thermoplastic resins. The cross sectional shape of the thigh engaging member and the calf engaging member is often elliptical giving the thigh engaging and calf engaging members optimal and maximal strength to weight characteristics. The elliptical cross sectional shape minimizes the bulk and profile to maintain rigidity of the thigh engaging member and the calf engaging member and minimizes the weight of the knee brace. The elliptical cross sectional shape of the thigh engaging member and the calf engaging member optimizes and maximizes the surface contact to the wearer's leg allowing the orthopedic brace to more securely hold the thigh and calf of the wearer.

In exemplary embodiments, the thigh engaging member and calf engaging member are each of unitary construction that imparts suitable rigidity to the thigh engaging member and calf engaging member. However, it will be apparent to those skilled in the art that various rigid, multi-member designs can also be implemented to construct useful thigh engaging members and calf engaging members within the invention. In those embodiments featuring a unitary construction the thigh engaging member and calf engaging member may be formed of molded, cast or machined metals, polymers, thermoplastic resins, composite material of molded metals, polymers, thermoplastic resins, fiber-reinforced polymers, fiber-reinforced thermoplastic resins and other suitable materials.

FIG. 5 provides an exploded view of an exemplary lateral hinge of the anatomically designed orthopedic knee brace for the right leg. The hinge has a first variable axis of rotation and comprises a first shell 37, a second shell 38, and a third shell 39 in the shape of a segment of a sphere. The first or inside shell 37 and third or outside 39 shell are concentric and fastened parallel to each other to form a first opening between them. The first/inside 37 shell and third/outside shell 39 have an extension 35, 36 fastened to the lateral portion 11 of the thigh engaging member 10. The second or center shell 38 has a first end designed to be inserted into the first opening, such that the first, second, and third shells are concentric and parallel. The second or center shell 38 has an extension 33, 34 fastened to the lateral portion 21 of the calf engaging member 20. The first 37 and third 39 shells are rotatably engaged to the second 38 shell by a plurality of cam follower pins and a plurality of cam slots. In an alternative embodiment of the invention, the first/inside shell and third/outside shell are fastened to the lateral portion of the calf engaging member, and the second/center shell is fastened to the lateral portion of the thigh engaging member.

The first and third shells are typically provided with a first extension 35, 36 fastened to the lateral portion of the thigh engaging member. The second shell is typically provided with a second extension 33, 34 fastened to the lateral portion of the calf engaging member. The first extension comprises an inner spherical plate extension 35 and an outer spherical plate extension 36 that are rigidly fastened to the lateral portion 11 of the thigh engaging member via fastener 40 connected to fastener boss 150. The second extension comprises a lateral retainer plate 33 and a center spherical plate extension 34 that are rigidly fastened to the lateral portion 21 of the calf engaging member via fastener 41 connected to fastener boss 152. In an alternative embodiment, the first extension is fastened to the lateral portion of the calf engaging member, and the second extension is fastened to the lateral portion of the thigh engaging member.

In more detailed aspects of the invention, the lateral hinge 30 has a lateral inner bushing 42 concentric and fastened parallel between the first/inner shell 37 and second/center 38 shell. The lateral hinge has a lateral outer bushing 43 concentric and fastened parallel between the second/center 38 and third/outer 39 shell. The lateral hinge has a lateral condyle base 44 generally concentric with and fastened parallel between the first/inner shell and the knee of the wearer. Fastener 45 holds the lateral condyle base, first/inner sphere, lateral inner bushing, second/center sphere, lateral outer bushing, and third/outer sphere. In a further detailed aspect, the medial hinge and the lateral hinge have concave surfaces facing the wearer's knee.

In other detailed aspects, the lateral hinge 30 has a first cam follower pin 46 located on the convex surface of the second/center spherical shell 38. The lateral hinge has a second cam follower pin 47 located on the convex surface of the third/outer spherical shell 39. A first cam slot 48 is located on the first/inner spherical shell 37 to receive the first cam follower pin 46. A second cam slot 49 is located on the second/center spherical shell 49 to receive the second cam follower pin 47. The first 37 and third 39 spherical shells are rotatably engaged to the second spherical shell 38 by means of the first 46 and second 47 cam follower pins moving within the first 48 and second 49 cam slots, respectively.

Figure 6:
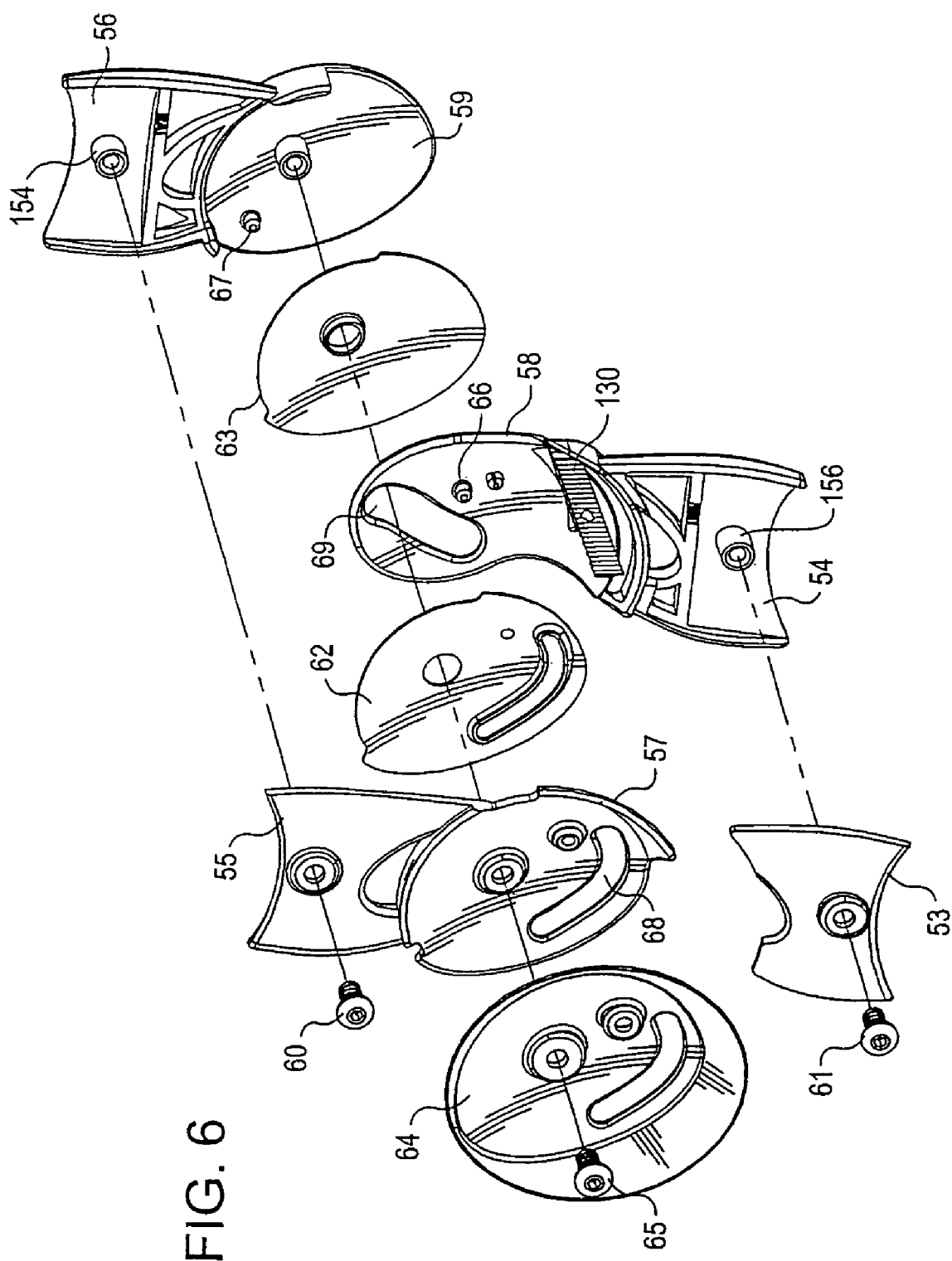
FIG. 6 is an exploded isometric view of the lateral hinge.

FIG. 6 provides an exploded view of a medial hinge of an anatomically designed orthopedic knee brace for the right leg. In certain two-hinge embodiments of the invention, the medial hinge 50 has a second variable axis of rotation and comprises a fourth shell 57, a fifth shell 58, and a sixth shell 59 in the shape of a segment of a sphere. The fourth or inside shell 57 and sixth or outside 59 shell are concentric and fastened parallel to each other to form a second opening between them. The fourth/inside 57 shell and sixth/outside 59 shell have extensions 55, 56 fastened to the medial portion of said thigh engaging member 10. The fifth or center shell 58 has a first end designed to be inserted into the second opening, such that the fourth, fifth, and sixth shells are concentric and parallel. The fifth or center shell 58 has extension 53, 54 fastened to the medial portion of the calf engaging member 20. In one embodiment, the fourth 57 and sixth 59 shells are rotatably engaged to the fifth 58 shell by a plurality of cam follower pins and a plurality of cam slots. In an alternative embodiment, the fourth/inside shell and sixth/outside shell are fastened to the medial portion of the calf engaging member, and the fifth/center shell is fastened to the medial portion of the thigh engaging member.

In other detailed aspects of the invention, the fourth 57 and sixth 59 shells are provided with a third extension 55, 56 fastened to the medial portion 13 of the thigh engaging member. The fifth 58 shell is provided with a fourth extension 53, 54 fastened to the medial portion 23 of the calf engaging member. The third extension comprises an inner spherical plate extension 55 and an outer spherical plate extension 56 that are rigidly fastened to the medial portion 13 of the thigh engaging member via fastener 60 connected to fastener boss 154. The fourth extension comprises a medial retainer plate 53 and a center spherical plate extension 54 that are rigidly fastened to the medial portion 23 of the calf engaging member. In an alternative embodiment, the third extension is fastened to the medial portion of the calf engaging member, and the fourth extension is fastened to the lateral portion of the thigh engaging member via fastener 61 connected to fastener boss 156.

In additional detailed aspects, the medial hinge 50 has a medial inner bushing 62 concentric and fastened parallel between the fourth/inner shell 57 and second/center 38 shell. The medial hinge has a medial outer bushing 63 concentric and fastened parallel between the fifth/center 58 and sixth/outer 59 shell. The medial hinge has a medial condyle base 64 concentric and fastened parallel between the fourth/inner sphere and the knee of the wearer. The medial condyle base, fourth/inner sphere, medial inner bushing, fifth/center sphere, medial outer bushing, and sixth/outer sphere are held by fastener means 65.

In related embodiments, the medial hinge 50 has a third cam follower pin 66 located on the convex surface of the fifth/center spherical shell 58. The medial hinge has a fourth cam follower pin 67 located on the convex surface of the sixth/outer spherical shell 59. A third cam slot 68 is located on the fourth/inner spherical shell 57 to receive the first cam follower pin 66. A fourth cam slot 69 is located on the second/center spherical shell 58 to receive the fourth cam follower pin 67. The fourth 57 and sixth 59 spherical shells are rotably engaged to the fifth spherical shell 58 by means of the third 66 and fourth 67 cam follower pins moving within the first 68 and second 69 cam slots, respectively.

In the exemplary embodiment shown in FIGS. 5 and 6, the orthopedic knee brace comprises a medial hinge having three parallel, concentric, spherical shells rotatably engaged by a plurality of cam follower pins in a plurality of cam slots, and a lateral hinge having three parallel, concentric, spherical shells rotatably engaged by a plurality of cam follower pins in a plurality of cam slots. In an alternative embodiment, the orthopedic knee brace may comprise a medial hinge having two parallel, concentric, spherical shells rotatably engaged by a plurality of cam follower pins in a plurality of cam slots, and a lateral hinge having two parallel, concentric, spherical shells rotatably engaged by a plurality of cam follower pins in a plurality of cam slots. Each hinge may have two or more cam follower pins rotatably engaging two or more cam slots. In an alternative embodiment, the orthopedic knee brace may comprise a medial hinge or a lateral hinge, each hinge having four parallel, concentric, spherical shells rotatably engaged by a plurality of cam follower pins in a plurality of cam slots.

Figure 7:
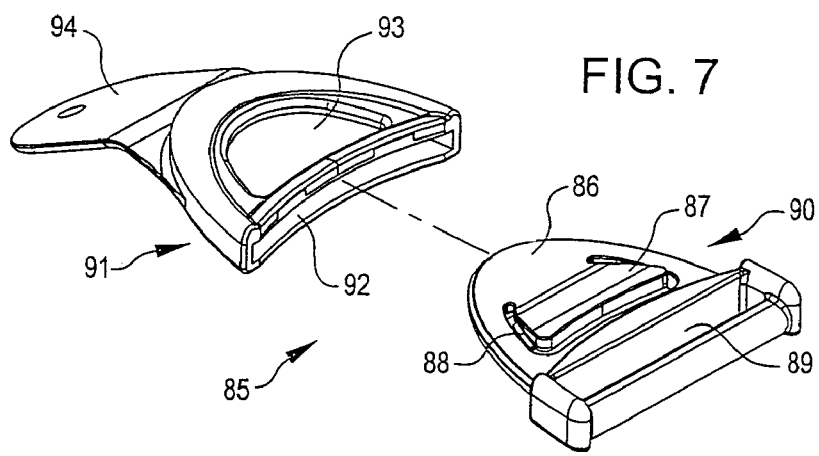
FIG. 7 is a perspective view of the buckle assembly.

FIG. 7 provides a perspective view of an exemplary buckle assembly for an anatomically designed orthopedic knee brace of the invention. This buckle assembly 85 allows the wearer to snap the straps 80, 81, 82, 83 in place and then tension the strap (see also FIG. 1). When removing the brace the wearer pushes a release button to release the strap. An advantage of the buckle assembly 85 is that it does not require the wearer to thread strap ends through d-rings or slots in the brace every time they don the orthopedic knee brace.

In more detailed embodiments, the anatomically designed orthopedic knee brace uses multiple buckle assemblies 85, 95, 100, 105 (see, e.g., FIG. 2). For example, two buckle assemblies 85, 95 may be attached to the lateral portion 11 of the thigh engaging member and two buckle assemblies 100, 105 attached to the lateral portion 21 of the calf engaging member. The buckle assembly typically comprises two main pieces: the female buckle 91 and the male buckle 90. The male buckle 90 comprises an extension 86 having a flat elliptical shape, buckle retention clip 87, retaining clip safety tabs 88, and buckle strap channel 89. The female buckle 91 comprises the male buckle receptacle 92, retention clip housing 93, and the buckle attachment extension 94. The male buckle extension 86 passes through the male buckle receptacle 92 and the two pieces are secured as the buckle retention clip 87 snaps into place within the buckle retention clip housing 93. The retention clip safety tabs 88 provide means for preventing the retention clip from coming out of the housing under load. The female buckle attachment extension 94 extends off the female buckle main body at an angle to conform to the wearer's leg. The male buckle strap channel 89 provides means for brace straps to pass through and adjust tension on the wearer's leg, thus securing the orthopedic knee brace to the wearer's leg. The wearer may push retention clip 87 to release the buckle assembly and thus remove the orthopedic knee brace from the wearer's leg.

Figure 8A:
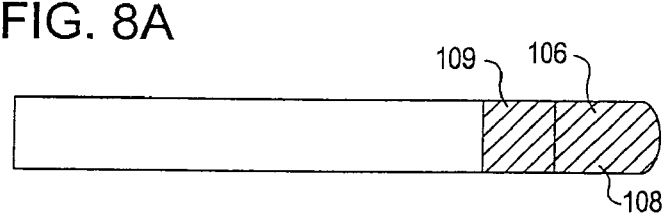
FIGS. 8A, 8B, 8C, and 8D are plan views of the strap construction.
Figure 8B:
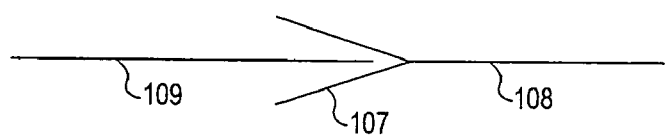
Figure 8C:
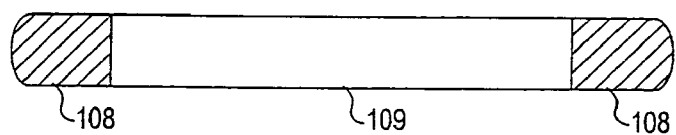
Figure 8D:
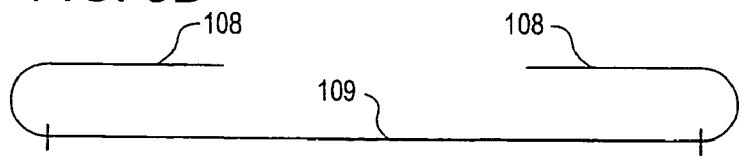

As illustrated in FIGS. 8A–8D, exemplary attachment systems of the orthopedic knee brace provide adjustable strap means for securing the orthopedic knee brace to the wearer's thigh and calf. This exemplary strapping system also controls the femur and tibia from unwanted motion between the orthopedic knee brace and the wearer's thigh and calf. The strapping material typically comprises at least a section of non-stretchable loop type of material containing an end section of hook type material 106 that allows the strap to reflect and secure back upon itself. FIG. 8A illustrates an alligator type of hook closure 107, which allows the user to remove and adjust the length of the strap by cutting and then re-apply the alligator closure to the end of the strap. FIG. 8B shows how the strapping system can be provided in multiple segments. For example, two straps are attached to the thigh engaging member and two straps are attached to the calf engaging member. The upper thigh strap 80 and the lower thigh strap 81 provide means to secure the thigh engaging member to the wearer's thigh. Both the upper thigh strap 80 and the lower thigh strap 81 are connected to attachment points on the inside of the medial portion 13 of the thigh engaging member. The upper thigh strap 80 traverses the back of wearer's thigh and is then slipped through the upper thigh strap buckle assembly 85 and connected back upon itself. The lower thigh strap 81 traverses the back of the wearer's thigh and is then slipped through the lower thigh strap buckle assembly 95 and connected back upon itself. The adjustment allows the wearer to tension the strap. Both upper and lower thigh strap buckle assemblies are attached to the lateral portion 11 of the thigh engaging member. The straps that provide means to secure the calf engaging member to wearer's leg are the upper calf strap 82 and the lower calf strap 83. Both upper and lower calf straps are attached to the medial portion 23 of the calf engaging member. The upper calf strap 82 traverses behind the calf and above the largest part of the calf musculature and is then slipped through the upper calf strap buckle assemble 100 and connected back onto itself. The lower calf strap 83 traverses behind the lower calf and is then slipped through the lower calf strap buckle assembly 105 and connected back onto it. The tibial strap 84 is made up of a generally non-stretchable loop material with tibial strap tabs 108 sewn to both ends. FIG. 8C illustrates an alternate embodiment wherein the tibial strap tabs have a hook material on one side and a loop material on the other allowing the tibial strap tabs to be secured to each other while overlapping each other. The tibial strap 84 runs through the medial tibial d-ring 109 and the lateral tibial d-ring 110 (see, e.g., FIG. 1). The tibial strap may be tensioned by the user to control the movement of the wearer's tibia in the calf engaging member.

It will be understood that other types of flexible securing means are useful in the present invention, including various flexible strap constructions. Alternatively, a substantially rigid overlapping adjustable strap assembly with a clamping mechanism will also be useful to secure the thigh engaging member and the calf engaging member to the thigh and calf of the wearer.

Figure 9A:
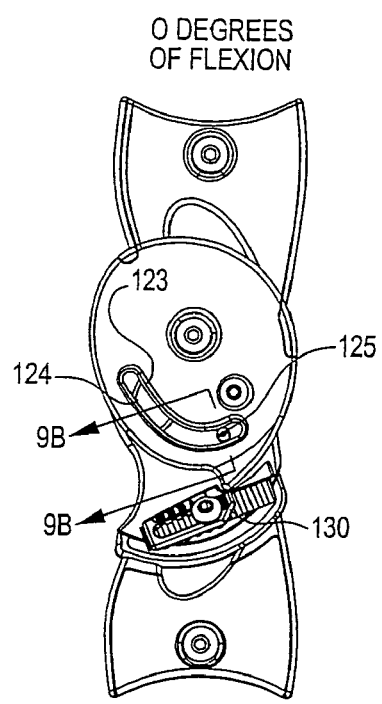
FIG. 9 is a perspective view (9A, 9C, and 9E) of a hinge and a cross sectional view (9B, 9D, and 9F) of a cam follower pin and cam slot at three positions of the pin in the slot during 0 degrees (9A, 9B), 20 degrees (9C, 9D), and 40 degrees (9E, 9F) of flexion of the wearer's leg in the anatomically designed orthopedic knee brace.
Figure 9B:
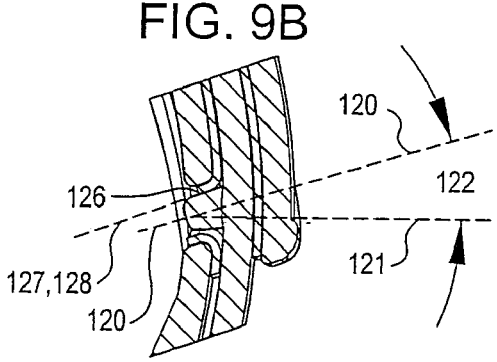
Figure 9C:
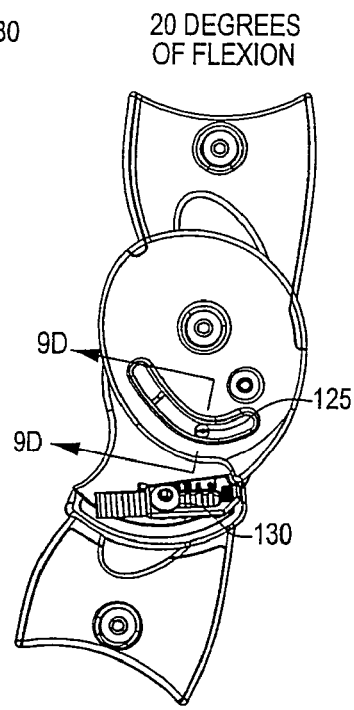
Figure 9D:
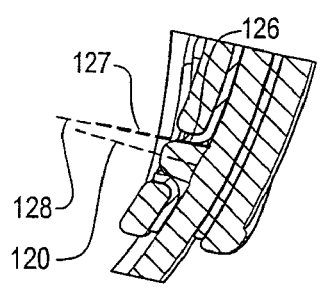
Figure 9E:
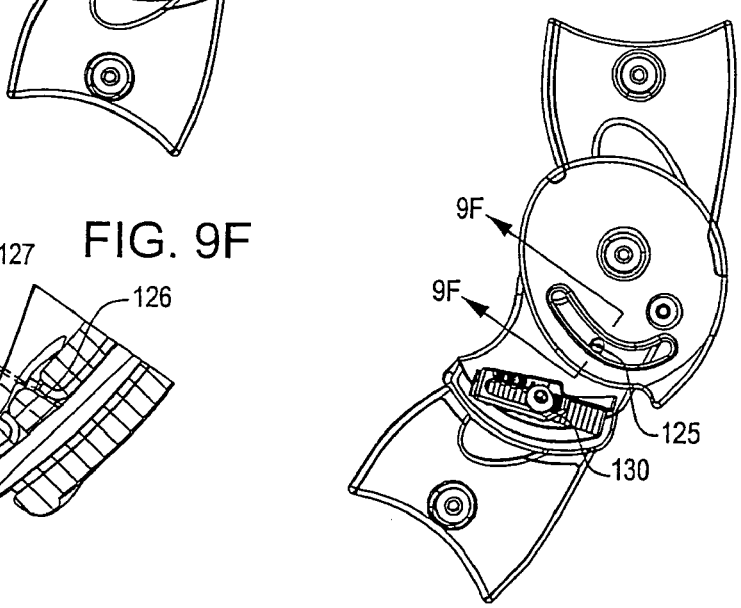
Figure 9F:
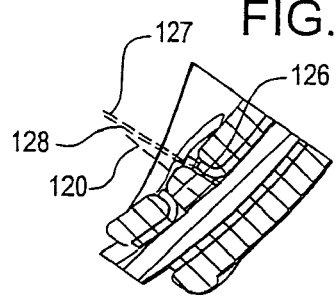

FIGS. 9A, 9C, and 9E provide perspective views of a hinge and an extension stop member at positions of flexion and extension of a wearer's knee within the brace. FIGS. 9B, 9D, and 9F provide cross sectional views of the cam follower pin in the cam slot at positions of flexion and extension of a wearer's knee within the brace. FIGS. 9B, 9D, and 9F show cross sections of the cam follower pin 125 within the hinge of the orthopedic knee brace typically having an edge 128 of a pin sidewall 126 at an angle 122 to the radial axis 121 of the spherical shell within the hinge. The cam slot within the spherical shell has an inner side wall 123 and an outer side wall 124. Cross sections 9B, 9D, and 9F of the cam follower pin 125 in the cam slot are shown, for example, at 0 degrees, 20 degrees and 40 degrees of flexion, respectively. In cross sections 9B, 9D, and 9F, an edge 127 of the cam slot inner side wall is closest to an edge 128 of the pin sidewall throughout the range of motion of flexion and extension of the orthopedic knee brace. The edge 127 of the cam slot inner side wall and the edge 128 of the pin side wall are parallel throughout the range of motion of flexion and extension of the orthopedic knee brace. Upon full flexion of the wearer's knee within the orthopedic knee brace the cam follower pin applies pressure to the outer cam slot wall 124. Upon full extension of the wearer's knee within the orthopedic knee brace the cam follower pin applies pressure to the inner cam slot wall 123. Two factors that may prevent wear and binding of the lateral and medial hinges during extended and intensive use of the anatomically designed orthopedic knee brace are (1) the angle 122 between the edge of the cam follower pin side wall 128 and the radial axis 121 of the spherical shell, and (2) the shape of the cam follower pin that allows edge 128 of the pin side wall to travel parallel to edge 127 of the cam slot inner side wall.

The angle 122 between the edge 128 of the cam follower pin sidewall and the radial axis 121 of the spherical shell of the hinge is typically between approximately 0 and 45 degrees. In other embodiments the angle 122 is between approximately 10 and 35 degrees. In yet additional embodiments, the angle 122 is between approximately 20 and 25 degrees.

Figure 10A:
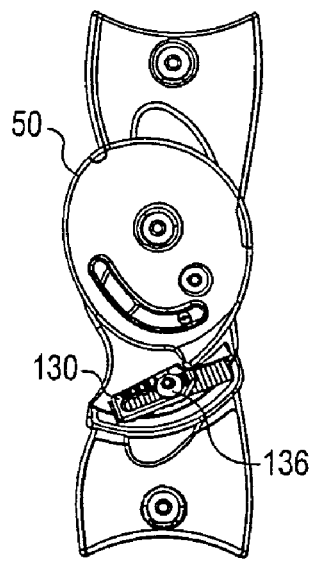
FIGS. 10A, 10B, 10C, and 10D are perspective views of the hinge and the extension stop member.
Figure 10B:
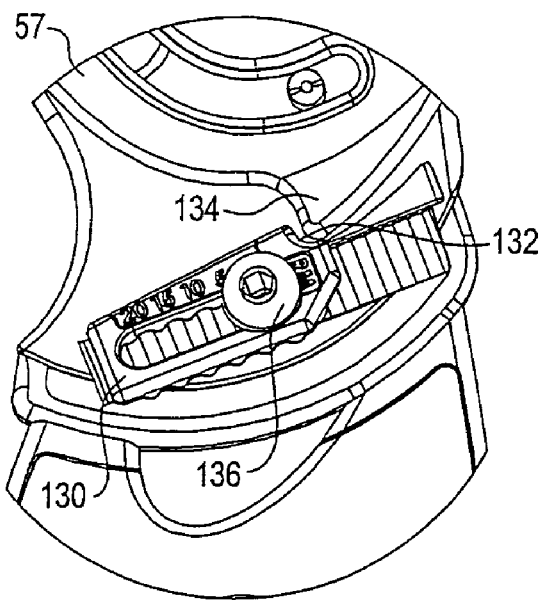
Figure 10C:
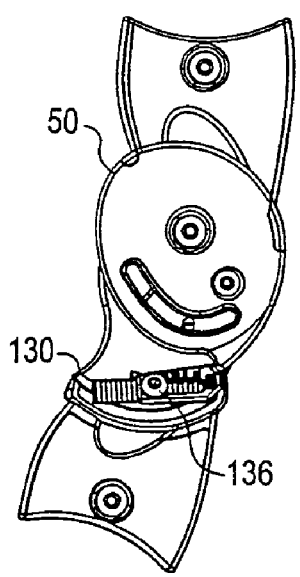
Figure 10D:
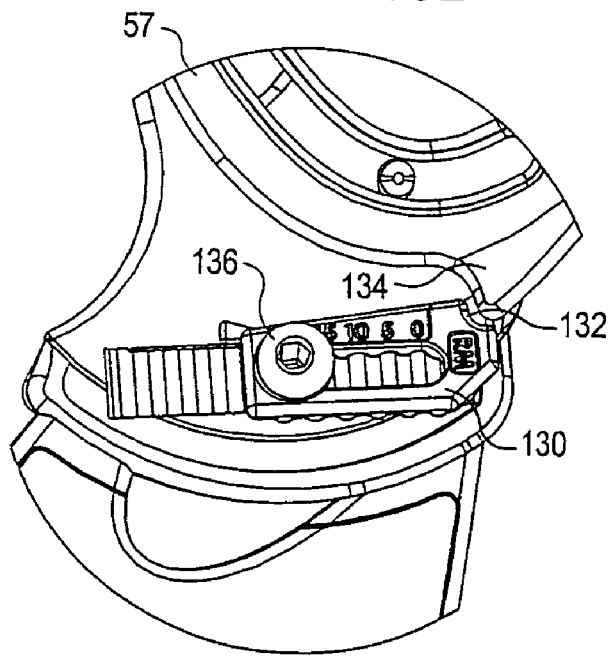

FIGS. 10A, 10B, 10C, and 10D show the extension stop member 130 on medial hinge 50. A comparable extension stop member exists on lateral hinge 70. The inner shell 57 of the hinge 50 has a catch 134. The catch contacts the extension stop 132 on the inner shell 57 of the hinge 50 to limit extension of the tibia relative to the femur of a wearer's leg when the leg is secured by the thigh engaging member and calf engaging member of the orthopedic knee brace. The extension stop member 130 is adjustable from a setting of 0 degrees to 20 degrees flexion in five degree increments by loosening set screw 136, moving the extension stop 132, and retightening set screw 136. The positional adjustments control the limits of extension of the wearer's leg from 0 degrees flexion (full extension) to 20 degrees flexion (partially limited extension). FIG. 10 shows two of the multiple positions for the extension stop member. FIGS. 10A and 10B show extension stop member 130 set at 0 degrees of flexion. FIGS. 10C and 10D show extension stop member 130 set at 20 degrees of flexion.

It will be understood by those skilled in the art that the basic structural elements of the lateral and medial hinges of the anatomically designed orthopedic knee brace in accordance with the present invention have been described. The hinge comprises parallel concentric shells designed with a spherical radius that provides optimal prescribing of the knee brace in six degrees of freedom of the wearer's knee. The cam follower pins and cam slots have been designed to provide optimal prescribing of six degrees of freedom of the wearer's knee. It will be understood that multiple designs of spherical shells, comprising two, three or four shells per hinge are within the scope of the present invention. It will be further understood that multiple designs of cam follower pins in cam slots of various arcuate or curved design or linear plus arcuate or curved design are within the scope of the present invention, and that multiple combinations of two or three cam follower pins in two or three cam slots within each hinge are contemplated herein. In one embodiment, the first, second and third shells of a lateral hinge have a spherical surface defining a first radius, and the fourth, fifth, and sixth shells of a medial hinge have a spherical surface defining a second radius.

FIG. 11 provides a cross sectional view of an exemplary lateral hinge of the anatomically designed orthopedic knee brace for the right leg. The lateral hinge comprises a first shell 37, a second shell 38, and a third shell 39 in the shape of a segment of a sphere. The first or inside shell 37 and third or outside 39 shell are concentric and fastened parallel to each other to form a first opening between them. The first/inside 37 shell and third/outside 39 shell have an extension 35, 36 fastened to the lateral portion 11 of the thigh engaging member 10. The second/middle shell 38 is between and concentric with the first and third shells. The second/middle shell 38 has an extension 33, 34 fastened to the lateral portion 21 of the calf engaging member 20. The values for the radii of the first, second and third shells of the lateral hinge is based upon an exemplary embodiment. Within exemplary embodiments, the values of the radii of the first, second and third shells of the lateral hinge range from approximately 2.5 inches to approximately 3.5 inches, alternatively, from approximately 2.8 inches to approximately 3.4 inches. In certain embodiments, the radii of the concentric shells correspond to C/R through N/R in FIG. 11.

In more detailed examples, the radius of the first shell 37 may be approximately 2.8 to approximately 3.1 inches, or may be approximately 2.96 to approximately 2.98 inches (for example, D/R may be 2.967 inches; E/R may be 2.972 inches) at its inside surface. In related examples, the radius of the first shell at its outside surface may be approximately 2.9 to approximately 3.2 inches, or may be approximately 3.06 to approximately 3.07 inches (for example, H/R may be 3.064 inches; F/R may be 3.067 inches). In an exemplary embodiment, the radius of the second shell 38 may be approximately 2.9 to approximately 3.2 inches, or may be approximately 3.09 to approximately 3.11 inches (for example, G/R may be 3.092 inches; I/R may be 3.103 inches.) at its inside surface. The radius of the second shell 38 at its outside surface may be approximately 3.1 to approximately 3.3 inches, or may be approximately 3.20 to approximately 3.21 inches (for example, J/R may be 3.203 inches; K/R may be 3.208 inches). In other detailed aspects, the radius of the third shell 39 may be approximately 3.1 to approximately 3.4 inches, or may be approximately 3.23 to approximately 3.24 inches (for example, N/R may be 3.236 inches; M/R may be 3.239 inches.) at its inside surface. The radius of the third shell 39 at its outside surface may be approximately 3.2 to approximately 3.5 inches, or may be approximately 3.33 inches to approximately 3.34 inches (for example, N/R may be 3.334 inches.). The value for radius M/R at the inside surface of the third shell 39 is based on studies and modeling of the human knee. The radius M/R at the inside surface of the third shell 39 corresponds to the radius value of the lateral femoral condyle of an average human male.

Figure 12:
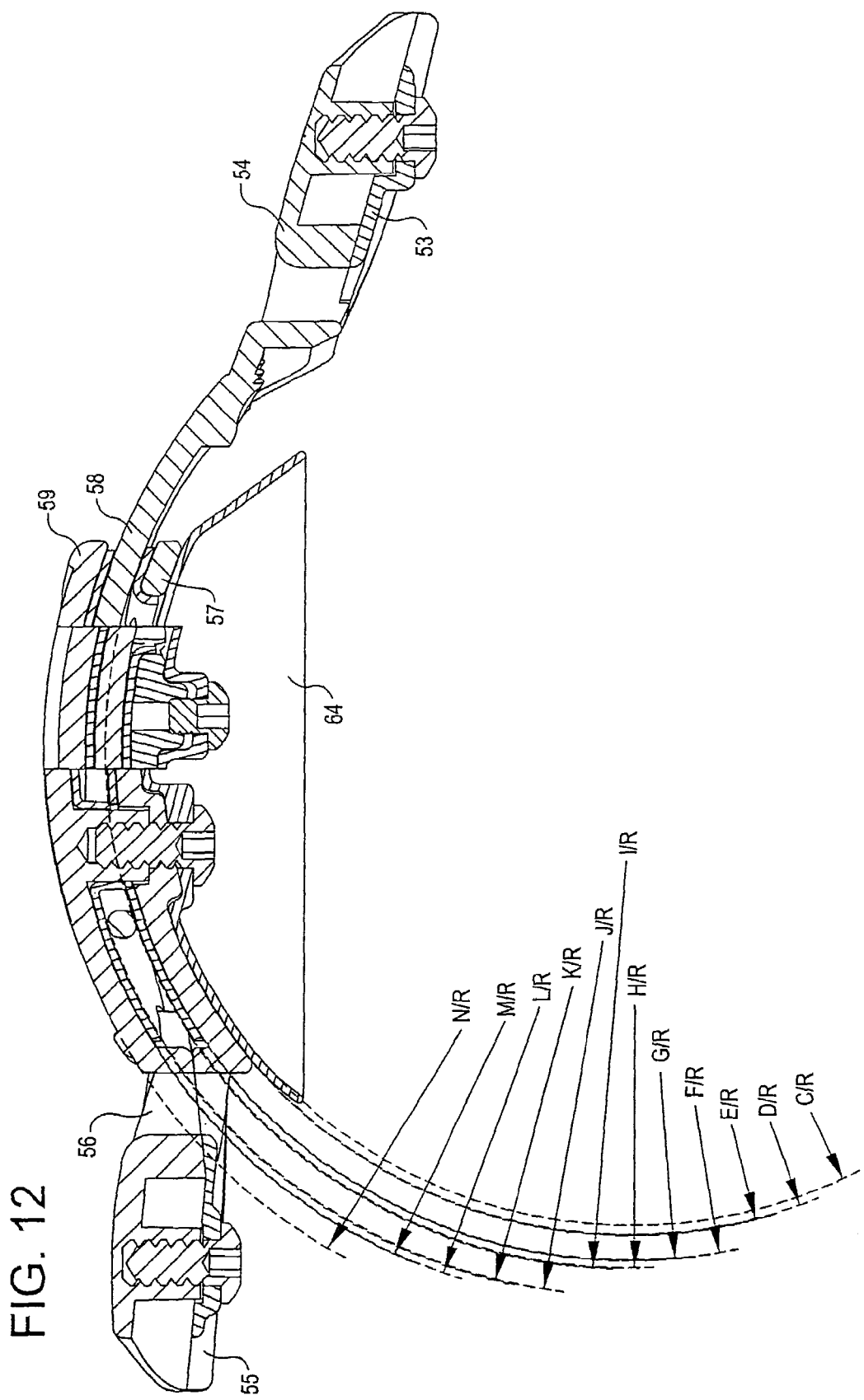
FIG. 12 is a cross sectional view of the lateral hinge.

FIG. 12 provides a cross sectional view of the medial hinge of the anatomically designed orthopedic knee brace for the right leg. The medial hinge comprises a fourth shell 57, a fifth shell 58, and a sixth shell 59 in the shape of a segment of a sphere. The fourth or inside shell 57 and sixth or outside 59 shell are concentric and fastened parallel to each other to form a second opening between them. The fourth/inside 57 shell and sixth/outside 59 shell have an extension 55, 56 fastened to the medial portion 13 of the thigh engaging member 10. The fifth/middle shell 58 is between and concentric with the first and third shells. The fifth/middle shell 58 has an extension 53, 54 fastened to the medial portion 23 of the calf engaging member 20. The values for the radii of the fourth, fifth and sixth shells of the medial hinge is based upon an exemplary embodiment. It is understood that the values of the radii of the fourth, fifth and sixth shells of the medial hinge may range from approximately 1.5 inches to approximately 2.5 inches, alternatively from approximately 1.8 inches to approximately 2.3 inches, within the scope of the anatomically designed orthopedic knee brace. In an exemplary embodiment, the radii of the concentric shells correspond to C/R through N/R in FIG. 12. In an exemplary embodiment, the radius of the fourth shell 57 may be approximately 1.7 to approximately 2.0 inches, or may be approximately 1.88 inches to approximately 1.89 inches (for example, D/R may be 1.880 inches; E/R may be 1.883 inches) at its inside surface. The radius of the fourth shell 57 at its outside surface may be approximately 1.8 to approximately 2.1 inches, or may be approximately 1.97 inches to approximately 1.99 inches (for example, F/R may be 1.978 inches; G/R may be 1.981 inches). In an exemplary embodiment, the radius of the fifth shell 58 may be approximately 1.9 to approximately 2.2 inches, or may be approximately 2.01 inches to approximately 2.02 inches (for example, H/R may be 2.009 inches; I/R may be 2.014 inches.) at its inside surface The radius of the fifth shell 58 at its outside surface may be approximately 2.0 to approximately 2.3 inches, or may be approximately 2.11 inches to approximately 2.12 inches (for example, J/R may be 2.114 inches; K/R may be 2.119 inches). In an exemplary embodiment, the radius of the sixth shell 59 may be approximately 2.0 to approximately 2.3 inches, or may be approximately 2.14 inches to approximately 2.16 inches (for example, N/R may be 2.147 inches; M/R may be 2.150 inches.) at its inside surface. The radius of the sixth shell 59 at its outside surface may be approximately 2.1 to approximately 2.4 inches, or may be approximately 2.24 inches to approximately 2.25 inches (for example, N/R may be 2.245 inches). The value for radius M/R at the inside surface of the sixth shell 59 is based on studies and modeling of the human knee. The radius M/R at the inside surface of the sixth shell 59 corresponds to the radius value of the medial femoral condyle of an average human male.

Figure 13:
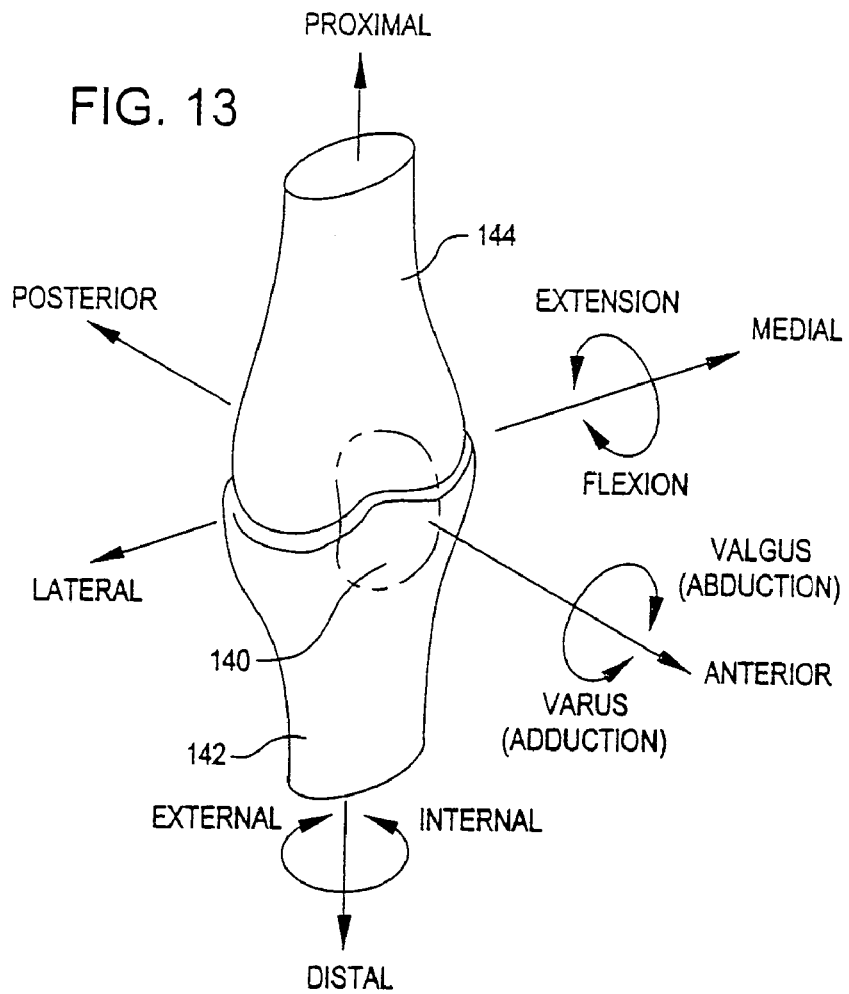
FIG. 13 is an anatomical figure of a wearer's leg showing six degrees of freedom of movement of a knee joint (formed by the interaction of a femur and a tibia) of the wearer's leg.

FIG. 13 provides a perspective view of a wearer's right leg illustrating the axes of movement of the tibia 142 with respect to the femur 144. The patella 140 is also shown. The anatomically designed orthopedic knee brace in accordance with the present invention prescribes asymmetric three-dimensional anatomic motion in six degrees of freedom. The three axes of rotation of the knee joint are flexion and extension, abduction and adduction, internal/external rotation between a femur and a tibia of a wearer's leg. The three axes of translation of the knee joint are anterior/posterior translation, medial/lateral translation, and proximal/distal translation between a femur and a tibia of a wearer's leg. Flexion and extension take place in the sagittal plane. During normal human locomotion the knee ranges from zero degrees, which is defined as full extension (straight leg), to an average of about 60 degrees of flexion (bent knee position). The natural roll and glide of the femur on the tibial plateau occurs in an anterior and posterior motion within the sagittal plane. As the femur rolls back on the tibia during flexion it also glides. Since the medial and lateral condyles are essentially spherical and have different radii, they rotate and glide at a different rate. The differential rollback creates a complex asymmetric motion to the knee. Further motion linked to the knee flexion and extension occurs in the frontal plane. As the knee flexes, the ankle moves toward the midline of the body to create adduction (or varus). As the knee extends, the ankle moves away from the midline of the body to create abduction (or valgus). Simultaneous motion also occurs in the transverse plane. The tibia exhibits internal and external rotation with respect to the femur. As the knee flexes the tibia internally rotates with respect to the femur. As the knee extends the tibia externally rotates. This phenomenon is known as "the screw home mechanism." The screw home motion is a result of ligament and other soft tissue tension, as well as the articular geometry and relationship between the medial and lateral femoral condyles with the respective tibial plateaus. As the knee flexes and extends, the tibia further exhibits proximal/distal motion and medial/lateral motion with respect to the femur.

Lateral Compression Test to Determine Rigidity and Flexibility of Knee Braces

Figure 14:
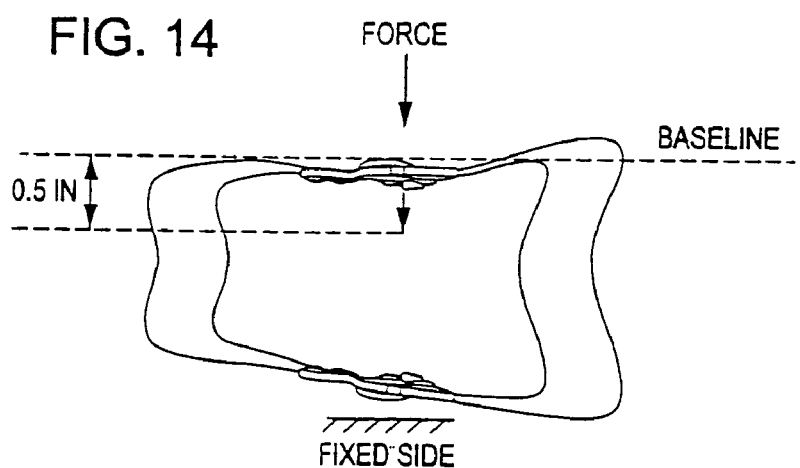
FIG. 14 is a front view of the orthopedic knee brace showing the direction of force applied to the knee brace in the lateral compression test for rigidity of the orthopedic knee brace.

In certain embodiments of the invention, for example two-hinge embodiments, the orthopedic knee brace, or one or more component(s) or interconnecting element(s) thereof, is/are rigid or substantially rigid, as measured, for example, by lateral rigidity using a lateral compression test. One illustrative purpose of the lateral compression test is to compare lateral rigidity between the orthopedic knee brace in accordance with the present invention and commercially available knee braces. The lateral compression test may be conducted, for example, by clamping the knee brace at either the medial or lateral hinge element. The hinge is placed on its side with one hinge element directly vertical above the second hinge element. One hinge element is fixed while a force is applied to the other hinge. A vertical pneumatic press is used to compress the opposing hinge elements toward each other by 0.5 inches off a baseline (see, e.g., FIG. 14). An inline load cell is used to determine the force required under load to compress the brace by 0.5 inches. The force is measured in units of pounds. It is understood in the art that there may be alternative measures of rigidity of the orthopedic knee brace.

TABLE 1

Rigidity as measured by lateral compression test: Force required to compress knee brace medial/lateral by 0.5 inches.

| Knee Brace | Force (pounds) |
|---|---|
| Medicus | 3.0 |
| Omni | 5.4 |
| Donjoy | 6.4 |
| Orthotech | 14.8 |
| BREG | 24.1 |
| Gen II | 26.6 |
| Donjoy "Defiance" | 26.7 |
| Lenox Hill | 32.2 |
| Townsend "Premier" | 39.4 |
| GTI | 96.2 |

Figure 15:
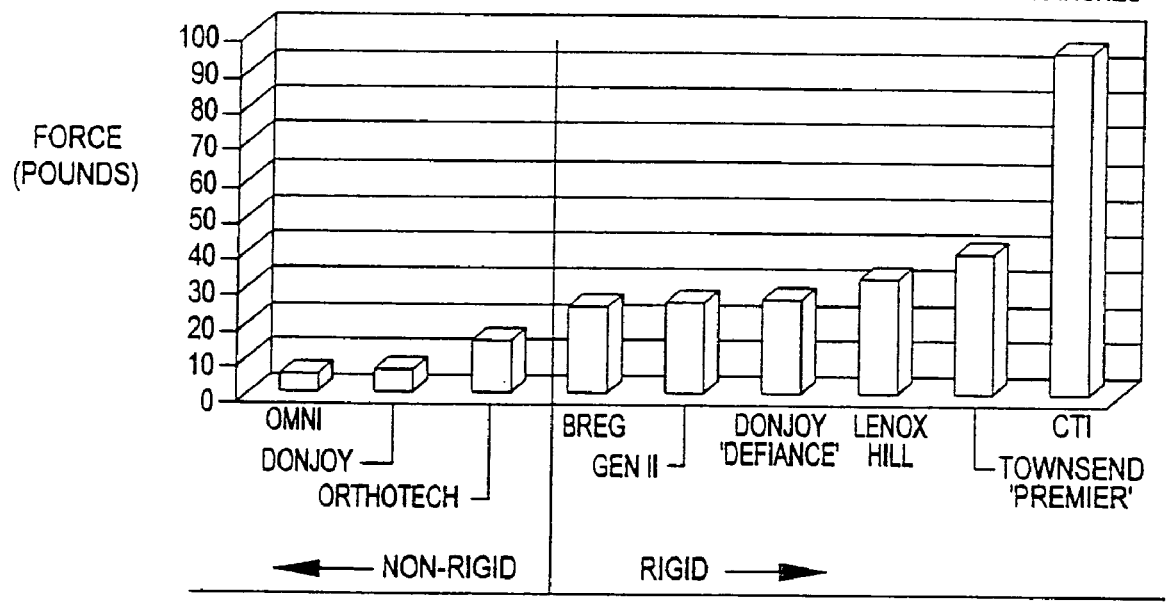
FIG. 15 is a graph of results of the lateral compression test on the orthopedic knee brace in accordance with the present invention compared to other knee braces.

Rigidity of an exemplary, two-hinge orthopedic knee brace may be determined, for example, by the degree of medial/lateral rigidity. Rigidity is measured as a function of the force required under load to compress the brace by 0.5 inches. Table 1 shows a range of rigidity in various commercial knee braces from approximately 3 pounds of force to approximately 96 pounds of force. FIG. 15 provides graphic results of the lateral compression test on the orthopedic knee brace in accordance with the present invention (e.g., designated as GEN II® brace) compared to other commercially available knee braces, indicating that rigid knee braces in accordance with the present invention typically require a force of 15 pounds or greater to compress medial and lateral hinges toward each other by a distance of 0.50 inches. In one embodiment, the orthopedic knee brace of the invention is rigid or substantially rigid if the force required under load to compress the brace by 0.5 inches is approximately 15 pounds or greater. In a further embodiment, the orthopedic knee brace is rigid or substantially rigid if the force required under load to compress the brace by 0.5 inches is approximately 25 pounds or greater. In a further embodiment, the force is approximately 30 pounds or greater. In a further embodiment, the orthopedic knee brace is rigid or substantially rigid if the force required under load to compress the brace by 0.5 inches is between approximately 25 pounds and approximately 35 pounds. Gen II is an exemplary embodiment of an anatomically designed orthopedic knee brace in accordance with the present invention.

In an alternative, single-hinge embodiment of the invention, the orthopedic knee brace, or a component or interconnecting element thereof, is flexible or substantially flexible if the force required under load to compress the brace by 0.5 inches is less than approximately 15. In other alternative embodiments, the orthopedic knee brace, component or interconnecting element is flexible or substantially flexible if the force required under load to compress the brace by 0.5 inches is approximately 10 pounds or less. In yet additional alternate embodiments, the brace, component or interconnecting element is flexible if the force required under load to compress the brace by 0.5 inches is between approximately 10 pounds and approximately 15 pounds. It is understood in the art that there may be alternative measures of rigidity or flexibility of the orthopedic knee brace.

Torque and Tension Test for Ligament Brace Hinge Screw Boss

The fastener and hinge extension fastener boss rigidly attach the lateral hinge extensions and medial hinge extensions to the thigh engaging member and the calf engaging member. Torque and tension tests were performed on the hinge extension fastener boss by tightening a high strength screw into the hinge extension fastener boss. In FIGS. 5 and 6 of the lateral and medial hinges, fasteners 40, 41, 60, 61 fasten into fastener bosses 150, 152, 154, 156 of the hinge extensions. The strength of the connection between the hinge extensions and the thigh engaging member and calf engaging member contributes to the rigidity of the orthopedic knee brace.

The hinge extension fastener boss was replicated on four different manufacturing process metals: cast aluminum alloy 383, cast magnesium alloy AZ91D, machined cast aluminum alloy 383, and machined wrought-aluminum 6061-T6. The fastener boss was tested in torque and tension with a screw fastener. The torque is tested by tightening a high strength screw with a round-beam torque wrench (in-lbs) until failure of the fastener boss occurs. The tension was tested using a load cell fixed to a 4:1 hinged lever arm. The load cell at one end of the lever arm records the maximum force (lbs) applied to the fastener boss at imminent failure. A screw was threaded into the fastener boss at the other end of the lever arm which is loaded in tension.

The thread on the cast magnesium is 6–32 where the thread on all other specimens is 8–32. An approximation is made to multiply the torque value of the 6–32 screw by a ratio of 1.188:1. This is possible because both threads have a pitch of 32 and the shear area becomes dependent on only the screw threads major diameter d. The major diameter of the 8–32 and 6–32 threads are 0.164 and 0.138 respectively which calculates to a 1.188:1 ratio.

The fasteners and hinge extension fastener bosses vary in size so it is important to relate the tension results between specimens in normal stress σ. The normal stress is defined by $$\sigma = \frac{F}{A} \quad (1)$$

where F is the force measured by the load cell and A is the cross sectional area of the boss (see Table 2). All the fasteners and fastener bosses use the thread major diameter and the outside diameter of the boss to calculate the area A. Equation 1 allows the force measured in tension to be recalculated by the ratio of the area of the two fasteners and fastener bosses of different diameters to match the design area. The design area used for the cross-sectional area of the boss is 0.036 inches$^2$. The recalculated force values using the design area can be seen in Table 2. The measured stress can be compared to the given ultimate tensile strength of the metals in Table 3. The ultimate tensile strength is the predicted failure stress point of the materials.

Hinge extension fastener bosses made of four different metal compositions withstood torque prior to failure: 60 in-lbs for cast aluminum, 35 in-lbs for cast magnesium, 50 in-lbs for machined cast aluminum, and 95 in-lbs for machined aluminum 6061-T6. Tensile tests resulted in 20,072 psi for cast aluminum, 19,120 psi for cast magnesium, 18,911 psi for machined cast aluminum, and 41,333 psi for machined aluminum 6061-T6.

TABLE 2

Forces and areas of specimens in tension

| | Type of Metal | | | |
|---|---|---|---|---|
| | Cast Aluminum Alloy 383 | Cast Magnesium AZ91D | Machined Cast Aluminum Alloy 383 | Machined Wrought-Aluminum 6061-T6 |
| Maximum Force Measured F (lb) | 1,003.6 | 382.4 | 680.8 | 1,488.0 |
| Measured Area A (in$^2$) | .050 | .020 | .036 | .036 |
| Maximum Force with Design Area | 722.6 | 688.3 | 680.0 | 1,4880.0 |

TABLE 3

Ultimate tensile strength of metal

| | Type of Metal | | | |
|---|---|---|---|---|
| | Cast Aluminum Alloy 383 | Cast Magnesium AZ91D | Machined Cast Aluminum Alloy 383 | Wrought-Aluminum Alloy 6061-T6 |
| Ultimate Tensile Strength $S_{ut}$ (psi) | 45,000 | 33,000 | N/A | 45,000 |

TABLE 4

Torque and Tension data between metals

| | Type of Metal | | | |
|---|---|---|---|---|
| | Cast Aluminum Alloy 383 | Cast Magnesium Alloy AZ91D | Machined Cast Aluminum Alloy 383 | Machined Wrought-Aluminum 6061-T6 |
| Failure Point in Compression | Threads Stripped | Boss Cracked Vertically | Boss Cracked Vertically | Threads Stripped |
| Measured Torque (in-lb) | 60 | 35 | 50 | 95 |
| Failure Point in Tension | Boss separated at bottom | Boss separated at bottom | Boss separated at bottom | Boss separated at bottom |
| Measured Tension (psi) | 20,072 | 19,120 | 18,911 | 41,333 |
| Percent Error | 55% | 42% | N/A | 8% |

Results indicate that fasteners and hinge extension fastener bosses constructed of wrought-aluminum 6061-T6 alloy surpassed all other metals in the torque and tension test. The fastener boss failure from torque between metals provides a good comparison analysis, but the fastener's material composition will influence the maximum torque applied to the boss. The screw used to test the boss was made of heat treated alloy steel which yields material properties greater than Grade 8. Because a corrosion resistant fastener is desired for the application, there is a likelihood of the fastener failing before the boss. For example an 18–8 stainless steel screw with a 6–32 thread will fail at about 33 in-lbs.

Fasteners and hinge extension fastener bosses constructed of cast aluminum alloy 383 have a high ultimate tensile strength in Table 3. However, cast aluminum alloy is not considered a homogenous material like that of the wrought-aluminum alloy 6061-T6. A large portion of the 55% error in the cast aluminum is most likely due to sensitivity in mold geometry and the voids that create inconsistencies in the grain structure of the material. The drilled and tapped thru hole in the fastener boss for both aluminum and magnesium cast materials must also be considered as a large contribution to error. The material properties supplied for any given material is most likely determined by testing unmodified prismatic bar specimens at the midsections where there is uniform deformation. These fasteners and hinge extension fastener bosses differ greatly from those having a threaded thru hole. The strength in a die cast is in the skin of the part. Therefore by threading a hole in the center of the fastener boss, the thread surface is weaker than the skin on the outside and is most likely the first location for failure from fracture. A cored hole in the die instead of drilling a hole in the boss after the die was made would provide the die cast skin strength at the screw.

Threaded Insert Pullout Test

The pull out strength of the threaded insert was measured. A pull out strength of at least 175 pounds is considered adequate for the threaded insert. The tests in Table 5 indicate that ColPlas brass insert, either cold pressed or molded has sufficient pull out strength for use in the orthopedic knee brace in accordance with the present invention. The brass insert is superior to the steel insert.

TABLE 5

Threaded Insert Pullout Test

| Threaded Insert | Frame Material | Insertion Method | Pull Strength |
| --- | --- | --- | --- |
| Steel PEM "SI press-in" | Machined Triax | Cold Pressed | 171 lbs. |
| ColPlas brass insert | Machined Triax | Cold Pressed | 192 lbs. |
| ColPlas brass insert | Injection Molded Triax | Molded in | 210 lbs. |

Range of Movement Data for an Anatomically Designed Orthopedic Knee Brace

During walking or running, the knee joint moves in six degrees of freedom, three rotational degrees and three translational degrees. The six degrees of freedom are flexion and extension, abduction and adduction, internal/external rotation, anterior/posterior translation, medial/lateral translation and proximal/distal translation between a femur and a tibia of a wearer's leg. During walking or running the knee flexes to about 20 to 30 degrees in some cases up to 60 degrees. See Reinschmidt C. Three-dimensional tibiocalcaneal and tibiofemoral kinematics during human locomotion—measured with external and bone markers. Ph.D. Thesis, The University of Calgary, Calgary, Canada, 1996. The complete flexion range of motion of the normal human knee about 0 degrees to 130 or 140 degrees. The orthopedic knee brace in accordance with the present invention has a flexion range of approximately −5 to approximately 135 degrees.

Studies on the medial-lateral translation patterns of the tibia during normal knee motion show a medial translation just after heel strike and as the knee flexes followed by lateral translation as the knee extends. See Reinschmidt C, et. al., *Gait and Posture*, 6: 98–109, 1997; Reinschmidt C., *Ph.D. Thesis*, The University of Calgary, Calgary, Canada, 1996; Reinschmidt C, et al., *Journal of Biomechanics* 30: 729–732, 1997, McClay I S., *Ph.D. Thesis*, The Pennsylvania State University, 1990. Other studies show a gradual pattern from lateral translation between full extension and 80 degrees flexion to a slight medial translation through the rest of the flexion range. See, e.g., Ishii Y, et al., *Clinical Orthopedics and Related Research:* 144–150, 1997; Lafortune M A, et al., *Journal of Biomechanics* 25: 347–357, 1992; Lafortune M A. The use of intra-cortical pins to measure the motion of the knee joint during walking. *Ph.D. Thesis*, The Pennsylvania State University, 1984; Lafortune M A, et al., *Journal of Orthopedics Research* 412–420, 1994, each incorporated herein by reference.

Figure 16:
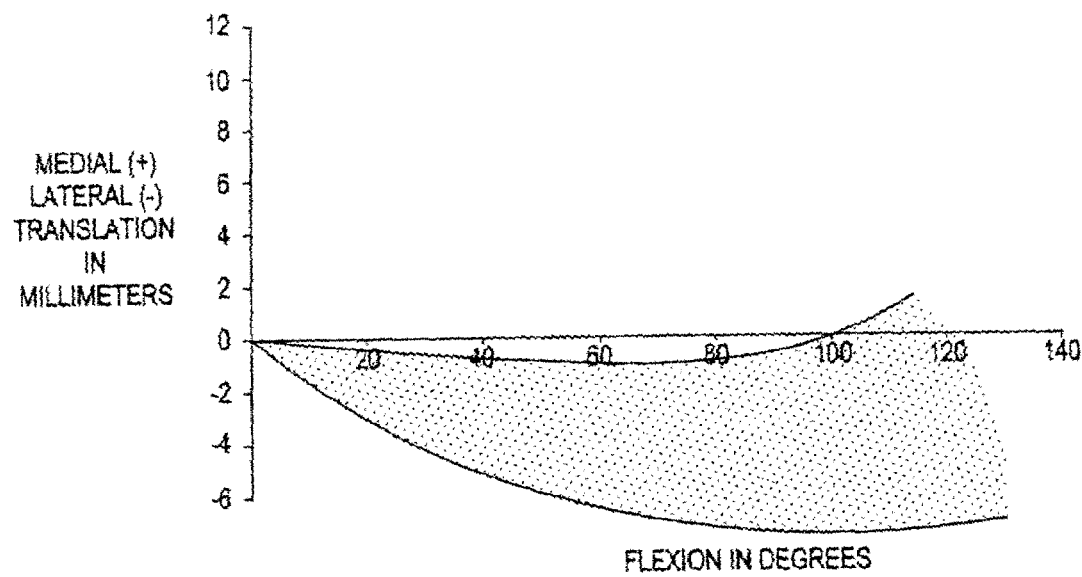
FIG. 16 is a graphic representation of medial lateral translation in millimeters during flexion and extension of a wearer's leg in the orthopedic knee brace in accordance with the present invention.

FIG. 16 shows medial lateral translation in degrees during flexion and extension of the orthopedic knee brace in an embodiment of the present invention (curved area). In one exemplary embodiment, the range of medial lateral translation during flexion and extension of the orthopedic knee brace is from approximately 2 millimeters of medial translation to approximately 6 millimeters of lateral translation through the range of flexion. In another exemplary embodiment, the orthopedic knee brace translates laterally up to approximately 4 millimeters as the knee flexes to approximately 80 degrees then translates medially approximately 1 millimeter through the rest of the flexion range.

Static studies of knee joint motion are carried out without force applied to the knee joint. Dynamic studies of knee joint motion are carried out with force applied to the knee joint. Among both the static and dynamic studies on knee joint motion, the maximum ranges of motion among some studies are shown to range from 12.5 millimeters of anterior movement of the tibia to 6.1 millimeters of movement posteriorly as the knee flexes. See, e.g., Marans H J, et al., *American Journal of Sports Medicine*, 17: 325–332, 1989; McClay I S., *Ph.D. Thesis*, The Pennsylvania State University, 1990, incorporated herein by reference. However, knees with ligament deficiency have an instability of the tibia in the anterior direction as the knee extends.

Figure 17:
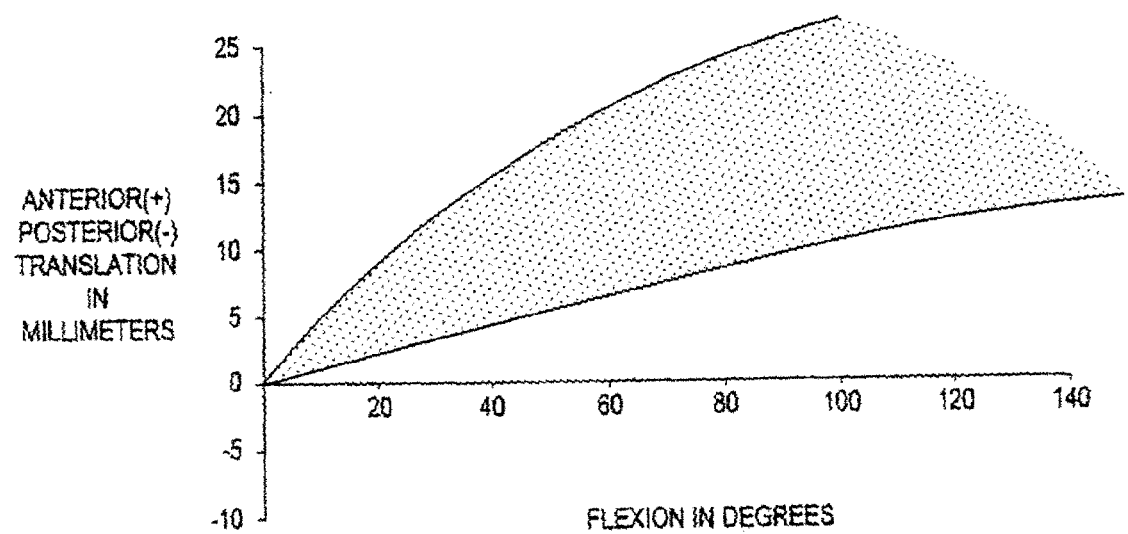
FIG. 17 is a graphic representation of anterior posterior translation in millimeters during flexion and extension of a wearer's leg in the orthopedic knee brace in accordance with the present invention.

FIG. 17 shows anterior posterior translation in millimeters during flexion and extension of the orthopedic knee brace in an embodiment of the present invention (curved area). The orthopedic knee brace translates posteriorly as the knee extends in order to counteract anterior drawer as the knee extends. In one exemplary embodiment, the orthopedic knee brace of the invention translates posteriorly approximately 25 millimeters as the knee extends. In another exemplary embodiment, the orthopedic knee brace translates posteriorly approximately 10 millimeters as the knee extends. In another exemplary embodiment, the orthopedic knee brace translates posteriorly between approximately zero millimeters and approximately 25 millimeters as the knee extends from full flexion. In yet another exemplary embodiment, the orthopedic knee brace translates posteriorly approximately 16 millimeters as the knee extends.

Studies have measured the proximal distal translation of the tibia while running and have shown that most of the compressive loading takes place at heal strike followed by distraction as the knee flexes. See, e.g., Marans H J, et al., *American Journal of Sports Medicine*, 17: 325–332, 1989;

McClay I S., *Ph.D. Thesis,* The Pennsylvania State University, 1990, incorporated herein by reference. Within the injured or deficient knee abrupt loading of the joint surfaces should be minimized.

Figure 18:
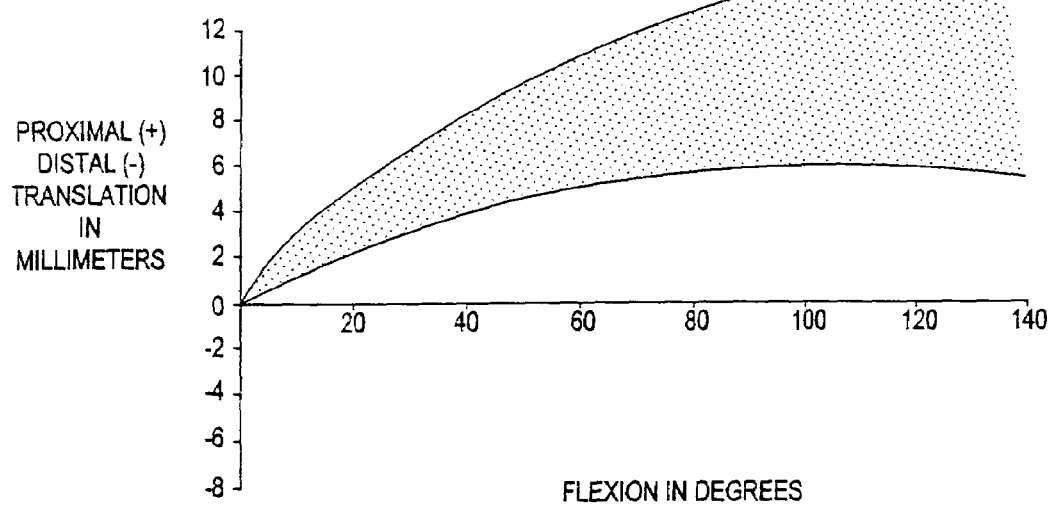
FIG. 18 is a graphic representation of proximal distal translation in millimeters during flexion and extension of a wearer's leg in the orthopedic knee brace in accordance with the present invention.

FIG. 18 shows proximal distal translation (compression distraction translation) in millimeters during flexion and extension of the orthopedic knee brace in an embodiment of the present invention. The orthopedic knee brace distracts distally as the knee extends. In one exemplary embodiment, the orthopedic knee brace distracts distally approximately 12 millimeters as the knee extends from full flexion. In another exemplary embodiment, the orthopedic knee brace distracts distally approximately 4 millimeters as the knee extends from full flexion. In another exemplary embodiment, the orthopedic knee brace distracts distally between approximately zero millimeters and approximately 12 millimeters as the knee extends from full flexion. In yet another exemplary embodiment, the orthopedic knee brace distracts distally approximately 6 millimeters as the knee extends from full flexion.

The reported magnitude of internal-external rotation varies among the available motion studies, from 3.5 degrees to over 20 degrees. Furthermore there are differences between the rotation patterns during walking and running gait and static motion. Studies that measured tibial rotation during running reported that the tibia externally rotated upon heel strike followed by an internal rotation up to mid-swing and then external rotation again through terminal-swing. See, e.g., Reinschmidt C, et. al., *Gait and Posture,* 6: 98–109, 1997; Reinschmidt C. Three-dimensional tibiocalcaneal and tibiofemoral kinematics during human locomotion-measured with external and bone markers. *Ph.D. Thesis,* The University of Calgary, Calgary, Canada, 1996; Reinschmidt C, et al., *Journal of Biomechanics* 30: 729–732, 1997, each incorporated herein by reference. The static studies however showed consistent internal rotation of the tibia through 80 or 90 degrees of flexion followed by slight external rotation through the remainder of the flexion range. In dynamic studies, the knee motion may be naturally perturbed with respect to motion of the static knee. The ligaments and joint surfaces work not only to control knee movement but also to absorb shock. For a healthy knee the induced stress on the knee ligaments is sustained during normal gait. For a ligament deficient knee these stresses could cause further damage.

Figure 19:
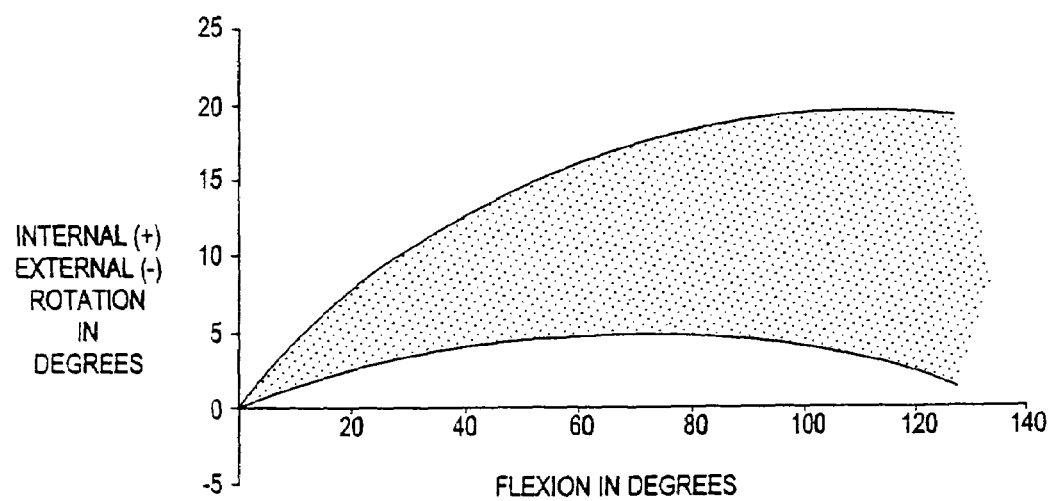
FIG. 19 is a graphic representation of internal external rotation in degrees during flexion and extension of a wearer's leg in the orthopedic knee brace in accordance with the present invention.

FIG. 19 shows internal external rotation in degrees during flexion and extension of the orthopedic knee brace in an embodiment of the present invention (curved area). The orthopedic knee brace of the invention mimics internal rotation patterns that occur when the knee moves statically through flexion. In one exemplary embodiment, the orthopedic knee brace internally rotates up to approximately 20 degrees as the knee flexes. In another exemplary embodiment, the orthopedic knee brace internally rotates up to approximately 4 degrees as the knee flexes. In another exemplary embodiment, the range of internal external rotation during flexion and extension of the orthopedic knee brace is from approximately zero degrees to approximately 25 degrees of internal rotation. In yet another exemplary embodiment, the orthopedic knee brace internally rotates up to approximately 10 degrees as the knee flexes.

Adduction-abduction (varus-valgus) rotation occurs while walking, running and static (no load) as the knee flexes and extends. The magnitude of rotation has been reported to be from 2 to 8 degrees. See, e.g., Marans H J, et al., *American Journal of Sports Medicine,* 17: 325–332, 1989; McClay I S. A comparison of tibiofemoral and patellofemoral joint motion in runners with and without patellofemoral pain. *Ph.D. Thesis,* The Pennsylvania State University, 1990, each incorporated herein by reference. In all cases, adduction (varus) rotation of the tibia with respect to the femur occurred as the knee flexed. This consistency is due to the fact that nearly every human knee embodies a smaller radius on the medial condyle compared to the radius of the lateral condyle. The dynamic studies have shown higher rotation than in the static studies which may be attributed to higher applied moments about the knee due to ground reaction force during gait. These perturbations may be minimized within the deficient or injured knee.

Figure 20:
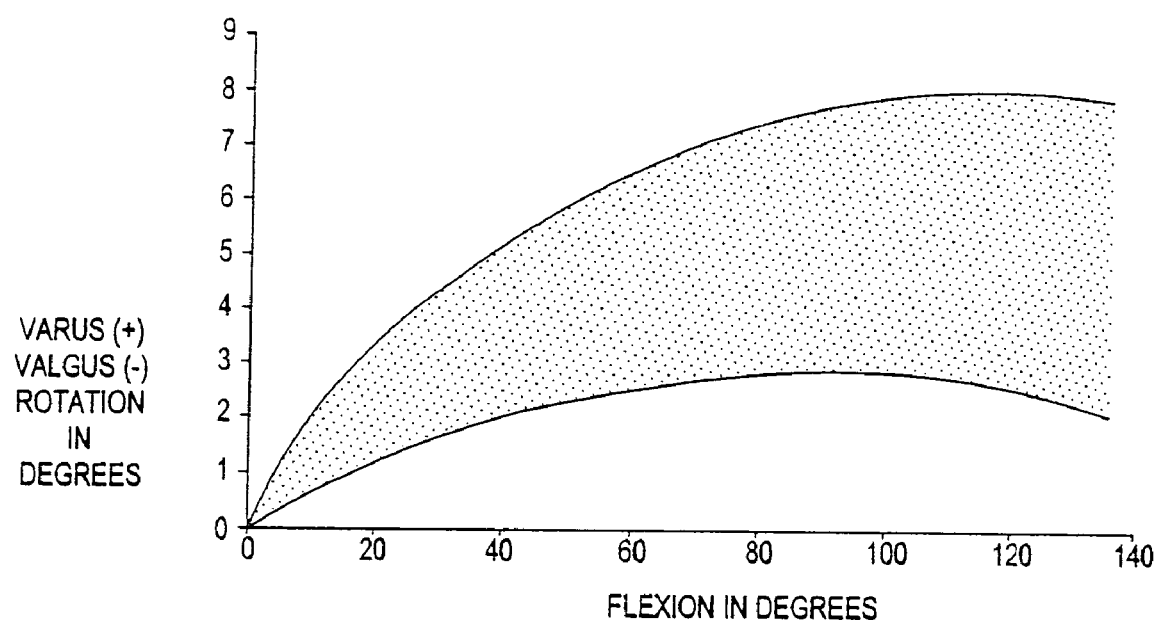
FIG. 20 is a graphic representation of varus valgus rotation in degrees during flexion and extension of a wearer's leg in the orthopedic knee brace in accordance with the present invention.

FIG. 20 shows varus valgus (adduction abduction) rotation in degrees during flexion and extension of an exemplary orthopedic knee brace of the invention (curved area). In one exemplary, the orthopedic knee brace exhibits varus (adduction) rotation up to approximately 2 degrees as the knee flexes. In another exemplary embodiment, the orthopedic knee brace exhibits varus (adduction) rotation up to approximately 8 degrees as the knee flexes. In another exemplary embodiment, the range of varus valgus rotation during flexion and extension of the orthopedic knee brace is from approximately zero degrees of varus rotation to approximately 10 degrees of varus rotation. In yet another exemplary embodiment, the orthopedic knee brace exhibits varus (adduction) rotation up to approximately 5 degrees as the knee flexes.

In certain embodiments of the invention, the knee brace is modified to have a unilateral hinge design useful for treatment, rehabilitation, and relief of symptoms associated with osteoarthritis of a wearer's knee. The orthopedic knee brace in accordance with this aspect of the invention is effective for treatment and relief of symptoms of medial or lateral unicompartmental osteoarthritis of the knee, treatment of tibial plateau fractures, osteochondritis dissecans, protection of meniscal allograft, and treatment of avascular necrosis of the medial femoral condyle. In additional embodiments, the single-hinge orthopedic knee brace of the invention is effective to correct varus/valgus misalignment.

Symptoms of osteoarthritis of the knee are, for example, pain and stiffness in the knee resulting from joint overuse and/or joint injury. Joint injury can lead to premature breakdown of articular and lunar cartilage within the femoraltibial compartment of the knee. In the case of osteoarthritis in the medial compartment, the cartilage breakdown is often accompanied by medial joint space narrowing and excessive varus alignment of the tibia with respect to the femur. Both mechanical and biological events may destabilize the normal coupling of degradation and synthesis of articular cartilage—these factors include morphologic, biochemical, molecular, biomechanical aspects, and joint pain. Alignment, malalignment, and biomechanics are intimately related and play an important role in pathology. Systemic factors may increase vulnerability to joint damage, most notably age (esp. female gender after age 50), genetic susceptibility and obesity. A variety of other systemic factors, such as nutrition and physical activity, also play a large role. Those systemic factors that increase systemic vulnerability to joint damage either work by or contribute to intrinsic joint vulnerability.

The orthopedic knee brace for treating or preventing symptoms of osteoarthritis comprises a unilateral hinge, wherein the knee brace prescribes asymmetric three-dimensional anatomic motion in six degrees of freedom between a femur and a tibia during flexion and extension of a wearer's leg, and wherein the knee brace is effective for treatment and relief of symptoms of osteoarthritis in a wearer's knee. In one embodiment, the unilateral hinge of the orthopedic knee brace is lateral to the wearer's knee. In an alternative embodiment, the unilateral hinge of the orthopedic knee brace is medial to the wearer's knee. The unilateral hinge of the orthopedic knee brace may comprise a unilateral hinge design. Alternatively, the unilateral hinge of the present invention may comprise two or more hinge mechanisms located either medial or lateral to a wearer's knee. The orthopedic knee brace within these aspects of the invention comprises a unilateral hinge, single or multiple hinge mechanism as described above for the two-hinge brace design that prescribes asymmetric three-dimensional anatomic motion in six degrees of freedom between a femur and a tibia during flexion and extension of a wearer's leg.

In more detailed aspects, the orthopedic knee brace for treating or preventing osteoarthritis comprises a thigh engaging member and a calf engaging member that are connected via a unilateral hinge or hinges. In exemplary embodiments, the orthopedic knee brace comprises a unilateral, lateral hinge or a medial hinge. In one embodiment, the orthopedic knee brace comprises a lateral hinge and is effective to relieve unicompartmental osteoarthritis affecting the lateral condyle of a wearer's knee. In alternate embodiments, the orthopedic knee brace for treating osteoarthritis comprises a medial hinge to relieve unicompartmental osteoarthritis affecting the medial condyle of a wearer's knee.

Within unilateral hinge brace designs of the invention, the thigh engaging member, the calf engaging member, the connections between the thigh and calf engaging members the medial or lateral hinge extensions, and the connections between the medial or lateral hinge extension and the unilateral hinge may be substantially "rigid", as described above, or "flexible". The thigh engaging member securely engages the wearer's thigh and is connected to the unilateral hinge. The calf engaging member securely engages the wearer's calf and is connected to the unilateral hinge. The connections between the thigh and calf engaging members and the medial or lateral hinge extensions and the connections between the medial or lateral hinge extension and the unilateral hinge allow the knee brace in accordance with the present invention to actively prescribe asymmetric three-dimensional anatomic motion between a femur and a tibia during flexion and extension of a wearer's leg. The connections between the thigh and calf engaging members and the medial or lateral hinge extensions and the connections between the medial or lateral hinge extension and the unilateral hinge further provide the ability of the hinge mechanism to actively prescribe motion of the knee in six degrees of freedom, three rotational degrees and three translational degrees. The connections between the thigh and calf engaging members and the hinge mechanism provide the ability of the orthopedic knee brace in accordance with the present invention to actively prescribe flexion and extension, abduction and adduction, internal/external rotation, anterior/posterior translation, medial/lateral translation and proximal/distal translation between a femur and a tibia of a wearer's leg.

In more detailed aspects, the single-hinge orthopedic knee brace in accordance with the invention comprises a lateral hinge or a medial hinge having a plurality of parallel, concentric shells in the shape of a segment of a sphere as described above for the two-hinge design. The shells have a plurality of cam follower pins and a plurality of cam slots. A side edge of the cam slot is parallel to a side of the cam follower pin. The cam follower pins are shaped to track the path of the cam slots from full flexion to full extension and prevent wear and binding of the lateral and medial hinges upon extended use by the wearer. An extension stop member is located on the inner shell on the lateral hinge or medial hinge. The extension stop members limit the movement of the orthopedic knee brace during flexion and extension of a wearer's leg. The extension stop member prevents over-flexion or over-extension of the wearer's leg while in the orthopedic knee brace. The inner shell of the hinge has a catch which contacts the extension stop on the extension stop member. Contact between the catch and the extension stop limits extension of the tibia relative to the femur of a wearer's leg when the leg is secured by the thigh engaging member and calf engaging member of the orthopedic knee brace. The extension stop member is adjustable from a setting of 0 degrees to 20 degrees flexion in five degree increments by loosening set screw, moving the extension stop, and retightening set screw. The positional adjustments control the limits of extension of the wearer's leg from 0 degrees flexion (full extension) to 20 degrees flexion (partially limited extension). Zero degrees flexion to 20 degrees flexion corresponds to the minimum angle of flexion of the wearer's leg while in the orthopedic knee brace in accordance with the present invention. In further embodiments, the extension stop member may limit extension of the wearer's leg to 30 degrees flexion, or alternatively, to 40 degrees flexion.

In a further detailed aspect of the single-hinge design, the plurality of cam follower pins engage the plurality of cam slots to rotatably engage the parallel, concentric, spherical shells. A side of the cam follower pin is shaped to track a path parallel to a side of the cam slot. In a further detailed embodiment, the side of the cam follower pin at a point closest to the cam slot is parallel to the side of the cam slot throughout the range of motion from flexion to extension of the knee brace.

In other detailed aspects, a side of the cam follower pin at a point closest to the cam slot, shaped to track a path parallel to a side of the cam slot, is at an angle to a radial axis of the spherical shell. In one aspect, the cam follower pin is essentially a cylinder, in which case a cross section of the cam follower pin describes a circle. In an alternate aspect, the cam follower pin is not cylindrical, in which case a cross section of the cam follower pin describes an ellipse or other closed curved structure or closed curve plus straight-sided structure. In an alternate aspect, the cam follower pin is multisided, in which case a cross section of the cam follower pin describes a polygon. In a further detailed embodiment, the angle between the side edge of the cam follower pin, shaped to track a path parallel to a side of the cam slot, and the radial axis of the spherical shell of the hinge is between approximately 0 and 45 degrees. In a further embodiment the angle is between approximately 10 and 35 degrees. In a further embodiment, the angle is between approximately 20 and 25 degrees. The cam follower pins are shaped to track the path of the cam slots from full flexion to full extension and prevent wear and binding of the lateral and medial hinges upon extended use by the wearer.

In more detailed aspects, the anatomical bracing hinge for treatment or relief of symptoms of osteoarthritis provides a medial hinge or a lateral hinge. In alternate embodiments, the lateral or medial hinge comprises a first shell, a second shell, and a third shell in the shape of a segment of a sphere. The first and third shells are concentric and fastened parallel to each other to form a first opening. The first and third shells are fastened to one of a lateral or medial portion of a thigh engaging member or a calf engaging member, and the second shell is fastened to the other of the lateral or medial portion of the thigh engaging member or calf engaging member. The second shell is designed to be inserted into the first opening. The second shell is concentric and parallel to the first and third shells. The first and third shells are rotatably engaged to the second shell by a plurality of cam follower pins engaging a plurality cam slots. The medial hinge or lateral hinge of the anatomical bracing hinge within this aspect of the invention actively prescribes asymmetric three-dimensional anatomic motion between a femur and a tibia during flexion and extension of a wearer's leg. In more detailed aspects, the medial hinge or the lateral hinge of the knee brace actively prescribes flexion and extension, abduction and adduction, internal/external rotation, anterior/posterior translation, medial/lateral translation, and proximal/distal translation between a femur and a tibia of a wearer's leg, as described above for the two-hinge brace design. Other aspects of the hinge and overall brace design and functional and performance specifications are also generally the same as described above for the two-hinge brace of the invention.

Figure 21:
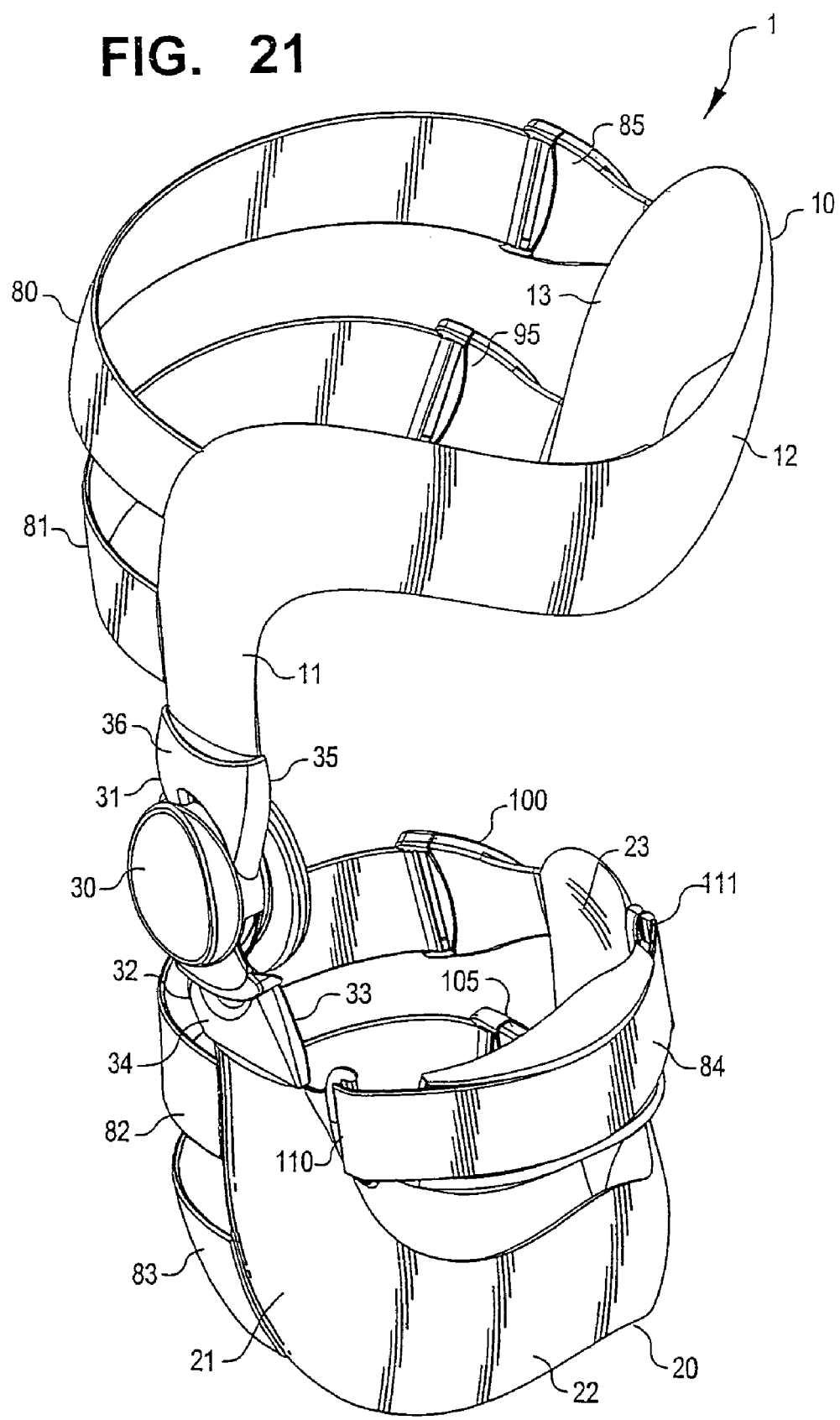
FIG. 21 is a side perspective view of an anatomically designed unilateral hinge orthopedic knee brace for treatment and prevention of osteoarthritis in accordance with the present invention.
Figure 22:
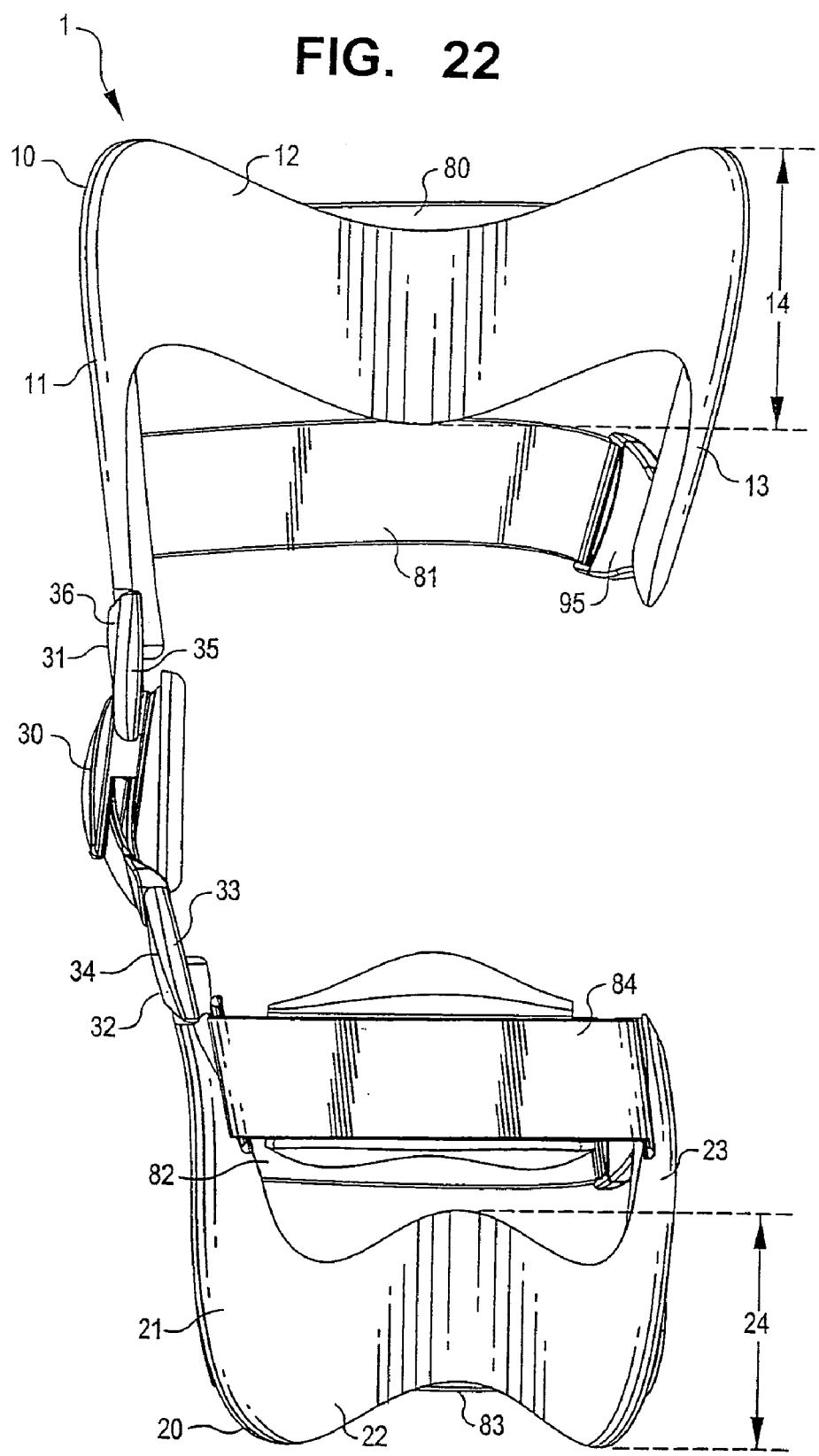
FIG. 22 is a front perspective view of an anatomically designed unilateral hinge orthopedic knee brace for treatment and prevention of osteoarthritis in accordance with the present invention.
Figure 23:
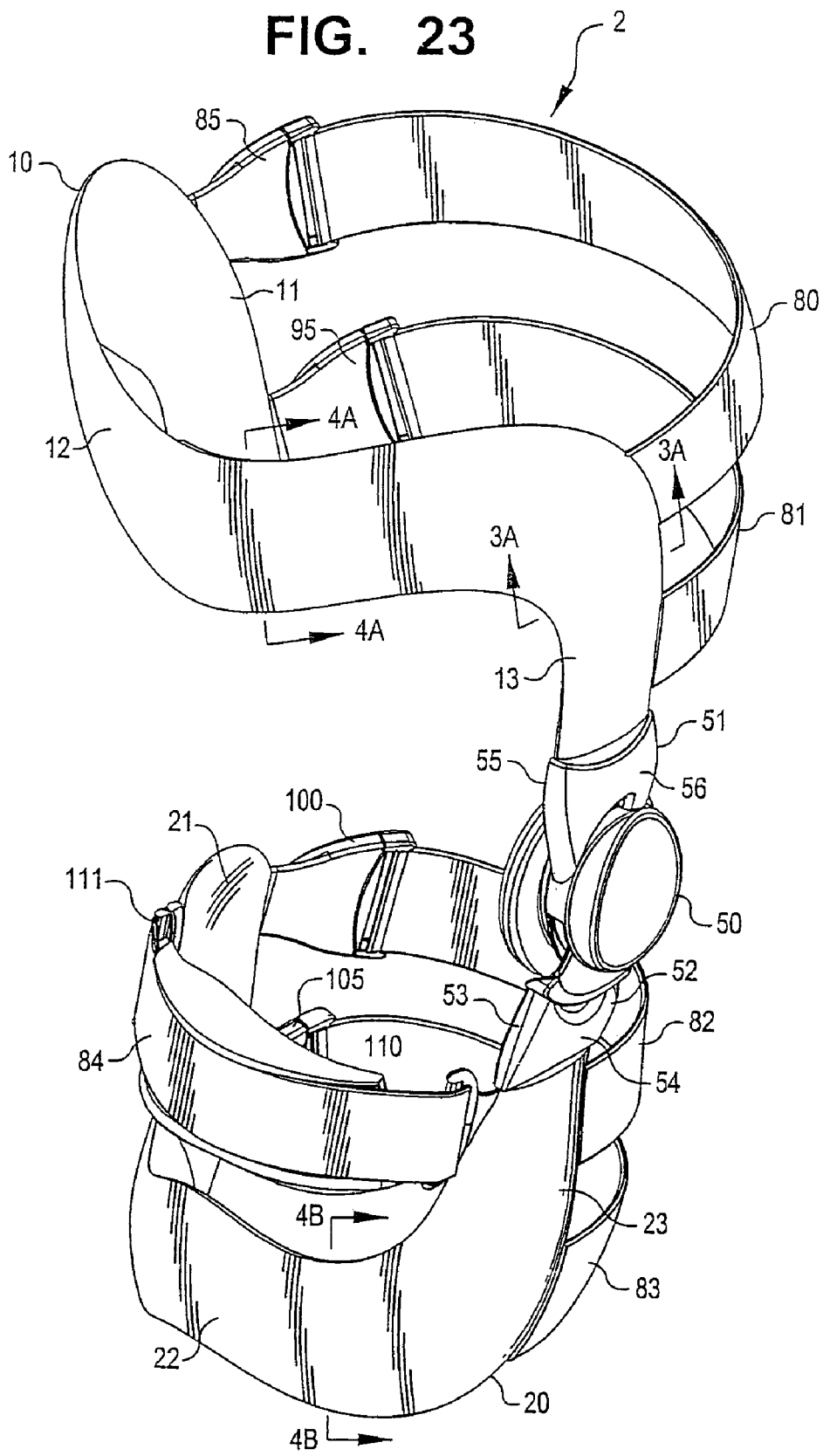
FIG. 23 is a side perspective view of an anatomically designed unilateral hinge orthopedic knee brace for treatment and prevention of osteoarthritis in accordance with the present invention.
Figure 24:
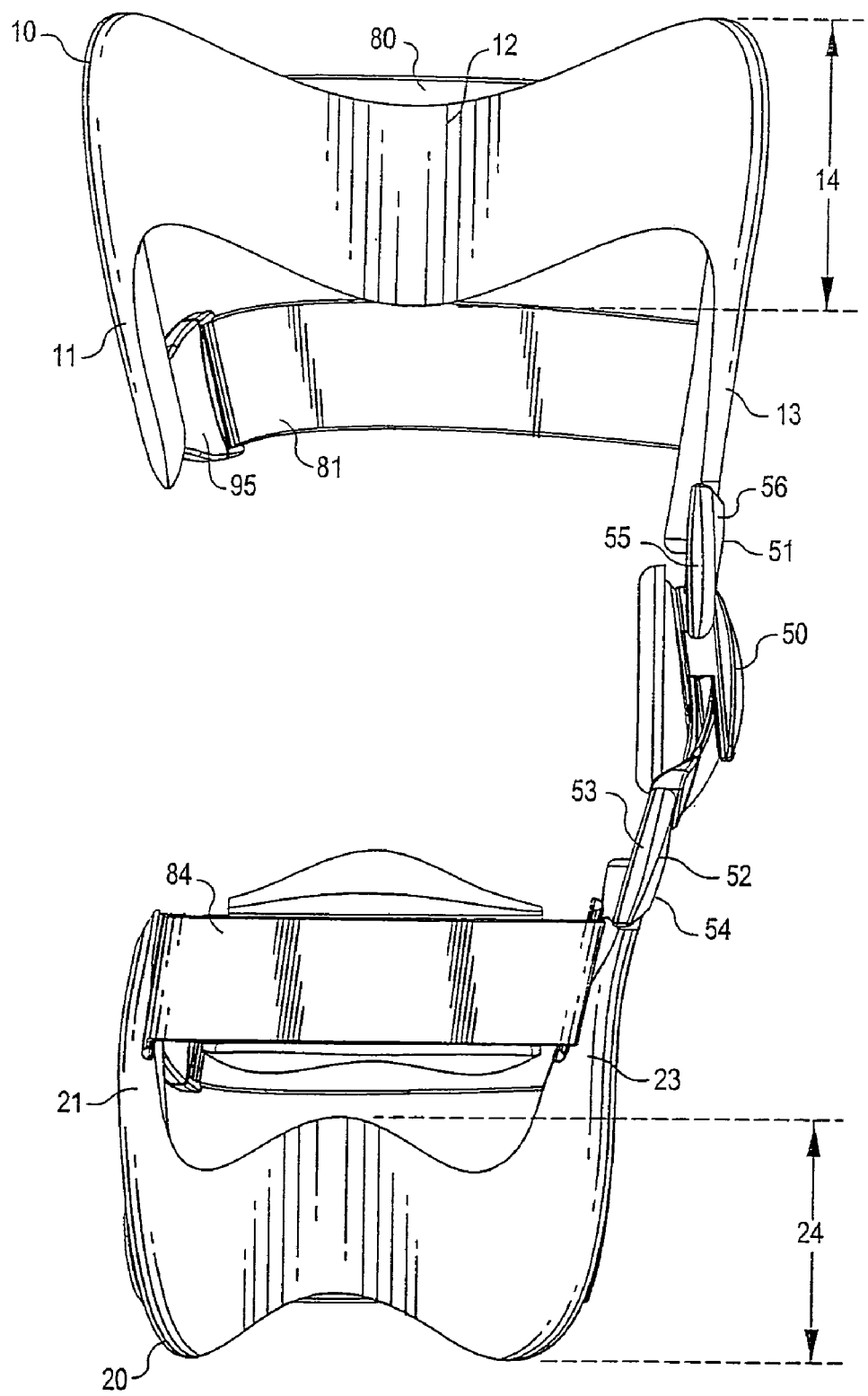
FIG. 24 is a front perspective view of an anatomically designed unilateral hinge orthopedic knee brace for treatment and prevention of osteoarthritis in accordance with the present invention.

FIGS. 21 and 22 provide perspective and frontal views, respectively, for an anatomically designed orthopedic knee brace for treatment and relief of osteoarthritis of the present invention comprising a lateral hinge in accordance with the present invention. FIGS. 23 and 24 show perspective and frontal views, respectively, for an anatomically designed orthopedic knee brace for treatment and relief of osteoarthritis of the present invention comprising a medial hinge in accordance with the present invention. In this description, only the orthopedic knee brace and hinge for the right leg are described. It is to be understood that the orthopedic knee brace for the left leg will be a mirror image of that described herein.

The anatomically designed orthopedic knee brace for treatment and prevention of osteoarthritis in accordance with the present invention is shown in FIGS. 21 through 24. The orthopedic knee brace shows a design of the brace and a connection of the thigh engaging member 10 and the calf engaging member 20 to the lateral hinge 30 (FIGS. 21 and 22) or to the medial hinge 50 (FIGS. 23 and 24). The thigh engaging member and the calf engaging member will often comprise a solid piece molded and formed to the contours of the wearer's thigh and calf. The thigh engaging member typically has a lateral 11, anterior 12, and medial 13 portion. The calf engaging member will typically have a lateral 21, anterior 22, and medial portion 23. The anterior portions of the thigh and calf engaging members are undulated to effectively control the soft tissue of the thigh or calf.

The thigh engaging member and the calf engaging member may be rigid or semi-rigid, as described above, a and may be constructed, for example, of reinforced fiber filled thermoplastic resin. The resin can be molded to provide a basic shape and later heated and formed to a desired shape, in this case, a human leg shape. In alternate embodiments, the thigh engaging member and the calf engaging member may be flexible or substantially flexible and may be constructed, for example, of a material that can be spring-loaded, for example, metal, plastic or fiberglass.

As used herein, the term "flexible", "substantially flexible", and "flexibly connected" refers to an orthopedic knee brace comprising a hinge that guides and restrains relative movement of a wearer's knee. In one exemplary embodiment, the orthopedic knee brace is considered "flexible", "substantially flexible", or "flexibly connected" if the force required under load to compress the brace by 0.5 inches in the medial lateral direction is less than 15 pounds as measured by the lateral compression test. In another exemplary embodiment, the force required is 10 pounds or less. In yet another exemplary embodiment, the orthopedic knee brace is flexible or substantially flexible if the force required under load to compress the brace by 0.5 inches is between approximately 10 pounds and approximately 15 pounds. It is understood in the art that there may be alternative measures of flexibility of the orthopedic knee brace, including measures described above that determine flexibility that is below the standard designated for "rigid" or "semi-rigid" braces, components, and interconnecting elements.

FIG. 25 provides a front perspective view of an exemplary, single-hinge knee brace 1 on a wearer's leg. In one exemplary embodiment, the orthopedic knee brace of the present invention for treatment and relief of symptoms of osteoarthritis comprises a dynamic force strap 140 that assists the orthopedic knee brace to apply three points of pressure 150, 152, 154 on the knee to create a reduction of pressure in the desired compartment of the lateral or medial condyle of the knee. The three points of pressure comprise three load forces: one force 150 applied by the thigh engaging member 10, a second force 152 applied by the calf engaging member 20, and an opposing force 154 applied by the dynamic force strap 140 on the side opposite the hinge 50. The dynamic force strap produces the contralateral third point of force. The dynamic force strap 140 attaches to the thigh engaging member 10 at one end and to the calf engaging member 20 at the other end. The dynamic force strap 140 spirals around the knee contacting and applying force to the side of the knee opposite to the side of the knee closest to the hinge of the orthopedic knee brace for treatment and relief of symptoms of unicompartmental osteoarthritis. The force applied by the dynamic force strap 140 occurs due to the fact that the length of the dynamic force strap remains constant, while the distance between the two attachment points of the strap on the thigh and calf engaging members becomes greater as the knee is extended. Extension of the knee causes the strap to tighten progressively during leg extension, producing an increasing force on the three points of pressure, 150, 152, 154 on the knee. The desired effect is the reduction in the load between the femoral condyle and the tibial plateau on the side of the knee (in the compartment requiring relief from osteoarthritis) next to the hinge of the knee brace. The effect of the dynamic force strap 140 is dynamic in that the three-point force system of the orthopedic knee brace of the present invention increases in intensity as the wearer extends the leg until maximum effect is realized at the point in the gait cycle where the wearer needs maximum assistance from the orthopedic knee brace. The orthopedic knee brace of the present invention provides a distinct advantage by providing a dynamic force from strap 140 that meets the changing needs of the wearer during gait and provides improved clinical and biomechanical outcomes. The orthopedic knee brace of the present invention is an improvement and contrasts to static force loads applied by other known knee braces.

The anatomically designed orthopedic knee brace for treatment and relief of symptoms of osteoarthritis in accordance with the present invention actively prescribes asymmetric three-dimensional anatomic motion between a femur and a tibia during flexion and extension of a wearer's leg in six degrees of freedom. In alternative embodiments, an anatomically designed orthopedic knee brace comprising a medial hinge or an anatomically designed orthopedic knee brace comprising a lateral hinge actively prescribes flexion and extension, abduction and adduction, internal/external rotation, anterior/posterior translation, medial/lateral translation, and proximal/distal translation between a femur and a tibia of a wearer's leg.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. Each of these references is incorporated herein by reference in its entirety for all purposes.

What is claimed is:

1. A unilaterally-hinged osteoarthritis knee brace comprising:
    a rigid thigh engaging member;
    a rigid calf engaging member; and
    a unilateral lateral hinge lateral to the wearer's knee, connecting said thigh engaging member to said calf engaging member;
    wherein said thigh engaging member and said calf engaging member form rigid connections to said lateral hinge,
    wherein said lateral hinge further comprises a plurality of parallel, concentric, spherical shells and a plurality of cam follower pins and a plurality of cam slots distributed among said shells, wherein said plurality of cam follower pins engage said plurality of cam slots to rotatably engage said shells, and wherein a side of each of said cam follower pins is shaped to track a path parallel to a side of each of said cam slots in which said pin is engaged,
    wherein said lateral hinge has a first variable axis of rotation and comprises:
    a first shell, a second shell, and a third shell in the shape of a segment of a sphere, said first and third shells being concentric and fastened parallel to each other to form a first opening, said first and third shells being fastened to a lateral portion of either said thigh engaging member or said calf engaging member, said second shell having a first end designed to be inserted into said first opening and a second end fastened to a lateral portion of the other of said said thigh engaging member or calf engaging member, said first and third shells rotatably engaged to said second shell by said plurality of cam follower pins and said plurality of cam slots;
    wherein said lateral hinge further comprises:
    a first cam follower pin and second cam follower pin distributed among said shells and extending inside said first opening, said first pin located on said second shell and said second pin located on said third shell, and a first cam slot and second cam slot distributed among said shells to receive said first and second pins, respectively, said first shell comprising said first cam slot and said second shell comprising said second cam slot,
    whereby, in use, when the wearer's leg is extended, said first variable axis of rotation is in alignment with the wearer's condyles, and wherein said knee brace prescribes asymmetric three-dimensional anatomic motion in six degrees of freedom by actively prescribing flexion and extension, abduction and adduction, internal/external rotation, anterior/posterior translation, medial/lateral translation, and proximal/distal translation between a femur and a tibia of the wearer's leg.

2. The orthopedic knee brace of claim 1, further comprising:
    an upper lateral hinge linkage forming a connection between said thigh engaging member and said lateral hinge; and
    a lower lateral hinge linkage forming a connection between said calf engaging member and said lateral hinge.

3. The orthopedic knee brace of claim 1, wherein the sides of said first and second cam follower pins at points closest to said first and second cam slots, respectively, are parallel to the sides of said first and second cam slots, respectively, throughout the range of motion from flexion to extension of said knee brace.

4. The orthopedic knee brace of claim 3, wherein the sides of said first and second cam follower pins at points closest to said first and second cam slots, respectively, form angles to a radial axis of said spherical shell.

5. The orthopedic knee brace of claim 4, wherein said angles are between approximately 0 and 45 degrees.

6. The orthopedic knee brace of claim 1, further comprising an extension stop member attached to said hinge to limit flexion and extension of the tibia relative to the femur of the wearer's leg.

7. The orthopedic knee brace of claim 6, wherein said extension stop member limits extension of the tibia relative to the femur to a minimum flexion angle between approximately 0 degrees and approximately 20 degrees.

8. The orthopedic knee brace of claim 1 further comprising:
    attachment means on said thigh engaging member to attach said thigh engaging member to a wearer's thigh;
    attachment means on said calf engaging member to attach said calf engaging member to a wearer's calf.

9. The orthopedic knee brace of claim 1, further comprising a dynamic force strap attaching said thigh engaging member and said calf engaging member to the wearer's leg.

10. The orthopedic knee brace of claim 1, wherein said hinge has a concave surface facing the knee.

11. The orthopedic knee brace of claim 1, wherein each of said thigh engaging member and said calf engaging member has a unitary construction.

12. The orthopedic knee brace of claim 11, wherein said unitary construction is molded construction.

13. The orthopedic knee brace of claim 11, wherein said unitary construction is laminated single body construction.

14. The orthopedic knee brace of claim 1, wherein said first and third shells further comprise a lateral inside shell and a lateral outside shell, said lateral inside shell having a first extension rigidly fastened to said lateral portion of said thigh engaging member, said lateral outside shell having a second extension rigidly fastened to said lateral portion of said thigh engaging member, said second shell having a third extension rigidly fastened to said lateral portion of said calf engaging member.

15. The orthopedic knee brace of claim 1, wherein said first, second and third shells have a spherical surface defining a first radius.

16. The orthopedic knee brace of claim 15, wherein said first radius is in a range from approximately 2.5 inches to 3.5 inches.

17. The orthopedic knee brace of claim 15, wherein said first radius is in a range from approximately 1.5 inches to 2.5 inches.

18. The orthopedic knee brace of claim 1 wherein said substantially rigid thigh engaging member and said substantially rigid calf engaging member are composed of a reinforced fiber filled thermoplastic resin.

19. The orthopedic knee brace of claim 1 wherein said lateral hinge is composed of a metal.

20. The orthopedic knee brace of claim 19, wherein said lateral hinge is composed of aluminum.

21. The orthopedic knee brace of claim 1 wherein said substantially rigid thigh engaging member and said substantially rigid calf engaging member are composed of a composite of reinforced fiber filled thermoplastic resin and metal.

22. The orthopedic knee brace of claim 1 wherein said lateral hinge is composed of a composite of reinforced fiber filled thermoplastic resin and metal.

23. A unilaterally-hinged osteoarthritis knee brace comprising:
    a rigid thigh engaging member;
    a rigid calf engaging member; and
    a unilateral medial hinge medial to the wearer's knee, connecting said thigh engaging member to said calf engaging member,
    wherein said thigh engaging member and said calf engaging member form rigid connections to said medial hinge,
    wherein said medial hinge further comprises a plurality of parallel, concentric, spherical shells and a plurality of cam follower pins and a plurality of cam slots distributed among said shells, wherein said plurality of cam follower pins engage said plurality of cam slots to rotatably engage said shells, and wherein a side of each of said cam follower pins is shaped to track a path parallel to a side of each of said cam slots in which said pin is engaged,
    wherein said medial hinge has a variable axis of rotation and comprises:
    a first shell, a second shell, and a third shell in the shape of a segment of a sphere, said first and third shells being concentric and fastened parallel to each other to form an opening, said first and third shells being fastened to a medial portion of either of said thigh engaging member or calf engaging member, said second shell having a first end designed to be inserted into said opening and a second end fastened to a medial portion of the other of said thigh engaging member or calf engaging member, said first and third shells rotatably engaged to said second shell by said plurality of cam follower pins and said plurality of cam slots;
    and wherein said medial hinge further comprises:
    a first cam follower pin and second cam follower pin distributed among said shells and extending inside said opening, said first pin located on said second shell and said second pin located on said third shell, and a first cam slot and second cam slot distributed among said shells to receive said first and second pins, respectively, said first shell comprising said first slot and said second shell comprising said second slot,
    whereby, in use, when the wearer's leg is extended, said second variable axis of rotation is in alignment with the wearer's condyles, and wherein said knee brace prescribes asymmetric three-dimensional anatomic motion in six degrees of freedom by actively prescribing flexion and extension, abduction and adduction, internal/external rotation, anterior/posterior translation, medial/lateral translation, and proximal/distal translation between a femur and a tibia of the wearer's leg.

24. The orthopedic knee brace of claim 23, further comprising:
    an upper medial hinge linkage forming a connection between said thigh engaging member and said medial hinge; and
    a lower medial hinge linkage forming a connection between said calf engaging member and said medial hinge.

25. The orthopedic knee brace of claim 23 wherein the sides of said first and second cam follower pins at points closest to said first and second cam slots, respectively, are parallel to the sides of said first and second cam slots, respectively, throughout the range of motion from flexion to extension of said knee brace.

26. The orthopedic knee brace of claim 25, wherein the sides of said first and second cam follower pins at points closest to said first and second cam slots, respectively, form angles to a radial axis of said spherical shell.

27. The orthopedic knee brace of claim 26, wherein said angles are between approximately 0 and 45 degrees.

28. The orthopedic knee brace of claim 23, further comprising an extension stop member attached to said hinge to limit flexion and extension of the tibia relative to the femur of the wearer's leg.

29. The orthopedic knee brace of claim 28, wherein said extension stop member limits extension of the tibia relative to the femur to a minimum flexion angle between approximately 0 degrees and approximately 20 degrees.

30. The orthopedic knee brace of claim 23 further comprising:
    attachment means on said thigh engaging member to attach said thigh engaging member to a wearer's thigh;
    attachment means on said calf engaging member to attach said calf engaging member to a wearer's calf.

31. The orthopedic knee brace of claim 23, further comprising a dynamic force strap attaching said thigh engaging member and said calf engaging member to the wearer's leg.

32. The orthopedic knee brace of claim 23, wherein said hinge has a concave surface facing the knee.

33. The orthopedic knee brace of claim 23, wherein each of said thigh engaging member and said calf engaging member has a unitary construction.

34. The orthopedic knee brace of claim 33, wherein said unitary construction is molded construction.

35. The orthopedic knee brace of claim 33, wherein said unitary construction is laminated single body construction.

36. The orthopedic knee brace of claim 23, wherein said first and third shells further comprise a medial inside shell and a medial outside shell, said medial inside shell having a first extension rigidly fastened to said medial portion of said thigh engaging member, said medial outside shell having a second extension rigidly fastened to said medial portion of said thigh engaging member, said second shell having a third extension rigidly fastened to said medial portion of said calf engaging member.

37. The orthopedic knee brace of claim 23, wherein said first, second and third shells have a spherical surface defining a radius.

38. The orthopedic knee brace of claim 37, wherein said radius is in a range from approximately 2.5 inches to 3.5 inches.

39. The orthopedic knee brace of claim 37, wherein said radius is in a range from approximately 1.5 inches to 2.5 inches.

40. The orthopedic knee brace of claim 23 wherein said substantially rigid thigh engaging member and said substantially rigid calf engaging member are composed of a reinforced fiber filled thermoplastic resin.

41. The orthopedic knee brace of claim 23 wherein said medial hinge is composed of a metal.

42. The orthopedic knee brace of claim 41, wherein said medial hinge is composed of aluminum.

43. The orthopedic knee brace of claim 23 wherein said substantially rigid thigh engaging member and said substantially rigid calf engaging member are composed of a composite of reinforced fiber filled thermoplastic resin and metal.

44. The orthopedic knee brace of claim 23 wherein said medial hinge is composed of a composite of reinforced fiber filled thermoplastic resin and metal.

* * * * *